US011877896B2

(12) United States Patent
Avalos et al.

(10) Patent No.: US 11,877,896 B2
(45) Date of Patent: Jan. 23, 2024

(54) STABILIZATION APPARATUSES AND METHODS FOR MEDICAL PROCEDURES

(71) Applicant: Cedars-Sinai Medical Center, Los Angeles, CA (US)

(72) Inventors: Pablo Avalos, West Hollywood, CA (US); Doniel Drazin, Los Angeles, CA (US); Clive Svendsen, Pacific Palisades, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 1028 days.

(21) Appl. No.: 16/685,140

(22) Filed: Nov. 15, 2019

(65) Prior Publication Data
US 2020/0253684 A1    Aug. 13, 2020

Related U.S. Application Data

(63) Continuation of application No. 14/888,076, filed as application No. PCT/US2014/036161 on Apr. 30, 2014, now Pat. No. 10,512,506.
(Continued)

(51) Int. Cl.
*A61B 90/11* (2016.01)
*A61B 17/02* (2006.01)
(Continued)

(52) U.S. Cl.
CPC .......... *A61B 90/11* (2016.02); *A61B 17/0206* (2013.01); *A61B 18/20* (2013.01);
(Continued)

(58) Field of Classification Search
CPC ..... A61B 17/0206; A61B 18/20; A61B 90/11; A61B 2090/374; A61B 2218/005;
(Continued)

(56) References Cited

U.S. PATENT DOCUMENTS 2,569,901 A    10/1951 Richard
3,817,249 A    6/1974 Nicholson
(Continued)

FOREIGN PATENT DOCUMENTS

CA    2239614 C    5/2005
CA    2910268 A1    11/2014
(Continued)

OTHER PUBLICATIONS

International Search Report and Written Opinion for PCT/US2014/036161 dated Aug. 27, 2014, 12 pages.
(Continued)

*Primary Examiner* — Baisakhi Roy
(74) *Attorney, Agent, or Firm* — Nixon Peabody LLP

(57) ABSTRACT

The present invention teaches minimally invasive apparatuses and methods for stabilizing and/or guiding medical instruments used in a variety of medical procedures, including (a) introducing one or more substances into a subject's body, (b) removing one or more substances from a subject's body, (c) manipulating a region of a subject's body, or (d) combinations thereof. Among the many advantages of the inventive apparatuses are their simplicity and adaptability to attach to a variety of retractors.

28 Claims, 25 Drawing Sheets

Related U.S. Application Data

(60) Provisional application No. 61/817,785, filed on Apr. 30, 2013.

(51) Int. Cl.
*A61B 18/20* (2006.01)
*A61B 90/50* (2016.01)
*A61B 90/00* (2016.01)
*A61B 90/57* (2016.01)
*A61B 17/34* (2006.01)
*A61B 10/04* (2006.01)
*A61B 18/00* (2006.01)

(52) U.S. Cl.
CPC ......... *A61B 90/50* (2016.02); *A61B 2010/045* (2013.01); *A61B 2017/0262* (2013.01); *A61B 2017/3405* (2013.01); *A61B 2018/00595* (2013.01); *A61B 2090/062* (2016.02); *A61B 2090/374* (2016.02); *A61B 2090/378* (2016.02); *A61B 2090/3762* (2016.02); *A61B 2090/571* (2016.02); *A61B 2218/005* (2013.01); *A61B 2562/0233* (2013.01); *A61B 2562/0271* (2013.01)

(58) Field of Classification Search
CPC ...... A61B 2562/0271; A61B 2010/045; A61B 2090/062; A61B 2090/3762; A61B 2018/00595; A61B 2017/3405; A61B 2017/0262; A61B 2090/378; A61B 2090/571; A61B 2562/0233; A61B 90/50
See application file for complete search history.

(56) References Cited

U.S. PATENT DOCUMENTS

| | | | |
|---|---|---|---|
| 4,467,791 A | 8/1984 | Cabrera et al. | |
| 5,647,373 A | 7/1997 | Paltieli | |
| 5,769,086 A | 6/1998 | Ritchart et al. | |
| 5,830,188 A | 11/1998 | Abouleish | |
| 6,139,493 A | 10/2000 | Koros et al. | |
| 6,270,481 B1 | 8/2001 | Mason et al. | |
| 6,322,500 B1 | 11/2001 | Sikora et al. | |
| 7,833,217 B2 | 11/2010 | Boulis | |
| 10,512,506 B2* | 12/2019 | Avalos | A61B 17/0206 |
| 2002/0133174 A1 | 9/2002 | Charles et al. | |
| 2003/0125753 A1 | 7/2003 | Saracione | |
| 2003/0199822 A1 | 10/2003 | Alchas et al. | |
| 2003/0208187 A1 | 11/2003 | Layer | |
| 2004/0181273 A1 | 9/2004 | Brasington et al. | |
| 2005/0152995 A1* | 7/2005 | Chen | A61K 31/19 424/722 |
| 2005/0193451 A1* | 9/2005 | Quistgaard | A61B 34/76 901/9 |
| 2006/0106416 A1 | 5/2006 | Douglas et al. | |
| 2006/0135945 A1 | 6/2006 | Bankiewicz et al. | |
| 2006/0224044 A1 | 10/2006 | Marchek et al. | |
| 2007/0123753 A1 | 5/2007 | Abdelgany et al. | |
| 2007/0233146 A1 | 10/2007 | Henniges et al. | |
| 2008/0183046 A1 | 7/2008 | Boucher et al. | |
| 2008/0188718 A1 | 8/2008 | Spitler et al. | |
| 2009/0036746 A1 | 2/2009 | Blackwell et al. | |
| 2009/0163808 A1* | 6/2009 | Peyrard | A61B 8/4281 601/4 |
| 2009/0287043 A1 | 11/2009 | Naito et al. | |
| 2010/0240989 A1 | 9/2010 | Stoianovici et al. | |
| 2010/0241136 A1* | 9/2010 | Doyle | A61B 34/71 606/130 |
| 2012/0010617 A1* | 1/2012 | Ramos Maza | A61B 17/8052 606/281 |
| 2012/0053573 A1 | 3/2012 | Alksnis | |
| 2012/0209110 A1 | 8/2012 | Bankiewicz et al. | |
| 2012/0226145 A1 | 9/2012 | Chang et al. | |
| 2012/0245431 A1* | 9/2012 | Baudouin | A61B 17/0206 600/219 |
| 2013/0066334 A1 | 3/2013 | Schoepp | |
| 2013/0068018 A1* | 3/2013 | Seeger | G01C 19/574 73/504.12 |
| 2013/0079799 A1 | 3/2013 | Kim et al. | |
| 2014/0058210 A1 | 2/2014 | Raymond et al. | |
| 2014/0066718 A1 | 3/2014 | Fiechter et al. | |
| 2014/0142422 A1 | 5/2014 | Manzke et al. | |
| 2014/0180249 A1 | 6/2014 | Solar et al. | |
| 2014/0243809 A1 | 8/2014 | Gelfand et al. | |
| 2016/0100897 A1 | 4/2016 | Avalos et al. | |
| 2018/0280611 A1 | 10/2018 | Avalos et al. | |
| 2019/0059869 A1 | 2/2019 | Avalos et al. | |

FOREIGN PATENT DOCUMENTS

| | | |
|---|---|---|
| CA | 2966029 A1 | 5/2016 |
| CA | 3003454 A1 | 5/2017 |
| CN | 1899229 A | 1/2007 |
| CN | 101123919 A | 2/2008 |
| CN | 102300512 A | 12/2011 |
| CN | 102379742 A | 3/2012 |
| CN | 202238111 U | 5/2012 |
| CN | 103561796 A | 2/2014 |
| CN | 103690205 A | 4/2014 |
| CN | 105338910 A | 2/2016 |
| CN | 107106814 A | 8/2017 |
| CN | 108289602 A1 | 7/2018 |
| DE | 10-2007-054317 A1 | 5/2009 |
| DE | 202012101617 U1 | 5/2012 |
| EP | 2991560 A1 | 3/2016 |
| EP | 3212271 A1 | 9/2017 |
| EP | 3367877 A1 | 9/2018 |
| HK | 1221389 A1 | 6/2017 |
| IN | 3085/MUMNP/2015 | 3/2016 |
| IN | 201727017050 A | 7/2017 |
| JP | 58-124456 A | 7/1983 |
| JP | 58-133246 A | 8/1983 |
| JP | 10-507938 A | 8/1998 |
| JP | 515372 A | 9/2001 |
| JP | 2005-524442 A | 8/2005 |
| JP | 2007-105392 A | 4/2007 |
| JP | 2008-515554 A | 5/2008 |
| JP | 2011-516205 A | 5/2011 |
| JP | 2014-386 A | 1/2014 |
| JP | 2016-522710 A | 8/2016 |
| JP | 2017-537679 A | 12/2017 |
| JP | 2018-535004 A | 11/2018 |
| JP | 6456924 B2 | 1/2019 |
| KR | 10-2016-0008209 A | 1/2016 |
| KR | 10-2017-0076705 A | 7/2017 |
| KR | 2018-0079346 A | 7/2018 |
| WO | 1998/039039 A1 | 9/1998 |
| WO | 2007/052975 A1 | 5/2007 |
| WO | 2011/156331 A2 | 12/2011 |
| WO | 2011/159733 A1 | 12/2011 |
| WO | 2014047540 A1 | 3/2014 |
| WO | 2014/179458 A1 | 11/2014 |
| WO | 2016/069936 A1 | 5/2016 |
| WO | 2017/075503 A1 | 5/2017 |

OTHER PUBLICATIONS

International Preliminary Report on Patentability for PCT/US2014/036161 dated Nov. 3, 2015, 11 pages.
EP 14791033.5 European Extended Search Report dated Aug. 25, 2016, 13 pages.
EP 15855587.0 European Extended Search Report dated Jul. 19, 2018, 6 pages.
International Search Report and Written Opinion for PCT/US2015/58134 dated Feb. 26, 2016, 15 pages.
International Preliminary Report on Patentability for PCT/US2015/58134 dated May 2, 2017, 12 pages.
International Search Report and Written Opinion for PCT/US2016/059539 dated Mar. 3, 2017, 16 pages.

(56) References Cited

OTHER PUBLICATIONS

Cole et al., Design of a Robotic System for MRI-Guided Deep Brain Stimulation Electrode Placement, 2009 IEEE International Conference on Robotics and Automation, 2009, pp. 4450-4456.
CN Office Action and Search Report for CN 2015800702505 dated Aug. 5, 2019, 13 pages.
CN Search Report for Appl. No. 2016800693500 dated Sep. 17, 2019, 13 pages.
EP 16860979.9 Extended European Search Report dated Mar. 26, 2019, 8 pages.

* cited by examiner

STABILIZATION APPARATUSES AND METHODS FOR MEDICAL PROCEDURES

CROSS-REFERENCE TO RELATED APPLICATION

This application claims the benefit of priority under 35 U.S.C. § 120 as a continuation of U.S. application Ser. No. 14/888,076, filed Oct. 29, 2015, which is the National Phase of International Application No. PCT/US2014/036161, filed Apr. 30, 2014, which designated the U.S. and that International Application was published under PCT Article 21(2) in English. This application claims priority under 35 U.S.C. § 119(e) to U.S. Provisional Application No. 61/817,785, filed Apr. 30, 2013, the contents of which are herein incorporated by reference in their entirety.

FIELD OF THE INVENTION

The present invention generally relates to apparatuses for medical procedures, and methods of use thereof.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

When physicians are performing procedures on or around certain areas of the body such as the spinal cord, brain, and joints, very precise, controlled, and stable manipulations are often required to avoid patient injury and to optimize outcome. There is a need in the art for apparatuses and methods that will improve the safety and accuracy of performing certain medical procedures in those areas.

More specifically, certain medical procedures performed by physicians are associated with especially high risks of accidental patient injury and/or treatment failure, due to a combination of the nature of the tissues involved in the procedure, the high degree of accuracy demanded by the procedure, limitations of existing surgical instruments (including stabilizing apparatuses), limitations associated with the field of view, and human error. In order to increase the likelihood of a favorable outcome, a number of attempts have been made to improve upon the stabilizing apparatuses used in conjunction with a number of medical instruments for a variety of different surgical procedures, including those involving the introduction of a substance into or removal of a substance from a delicate area of a patient's body. Exemplary stabilizing apparatuses known in the art include the Spinal Derrick, the Warner Device, and the Brundobler Device. Unfortunately, these devices are all either difficult to use (requiring a large amount of physician training), have an excessive part count (thereby carrying a relatively high risk of equipment failure or patient injury), or have significant problems related to positioning. For example the Spinal Derrick device used for spinal surgery comprises over 50 parts, making its assembly long and difficult, and leading to an increased risk of one of its parts falling into the incision and causing spinal cord trauma. Additionally, this device lacks accurate scales, and requires the use of four percutaneous posts that are placed "blindly," further increasing the risk of spinal cord injury, infection, and bleeding (partly due to the four additional incisions required).

SUMMARY OF THE INVENTION

In various embodiments, the invention teaches an apparatus that includes a securing arm that includes a first end, a second end, a long axis, and a short axis; a connecting arm that includes a first end, a second end, a long axis, and a short axis; a positioning arm that includes a first end, a second end, a long axis, and a short axis; and a guiding arm that includes a first end, a second end, a long axis, and a short axis; wherein (1) the first end of the connecting arm is attached to the second end of the securing arm, (2) the second end of the connecting arm is attached to the first end of the positioning arm, (3) the long axis of the connecting arm is perpendicular to the long axis of each of the securing arm and positioning arm, (4) the first end of the securing arm and the second end of the positioning arm can be positioned to extend in substantially the same direction away from the connecting arm, (5) the positioning arm is attached at its second end to the second end of the guiding arm, such that the positioning arm and guiding arm are perpendicular to one another, and (6) the guiding arm can be positioned such that the axis along which its long axis is situated is perpendicular to but does not intersect with the axes along which the long axis of the securing arm and the long axis of the connecting arm are respectively situated. In some embodiments, the securing arm further includes one or more clamps on its first end, and the one or more clamps are configured to attach to an arm of a tissue retractor. In some embodiments, the guiding arm further includes an instrument attaching component configured to slide along the long axis of the guiding arm. In some embodiments, the instrument attaching component includes one or more clamps configured to clamp a medical instrument. In certain embodiments, the sliding motion of the instrument attaching component is controlled by a dial situated at the first end of the guiding arm. In some embodiments, the connecting arm includes elongated nesting elements that allow for telescoping motion in the direction of its long axis, such that the length of the connecting arm can be increased or decreased. In certain embodiments, the positioning arm includes elongated nesting elements that allow for telescoping motion in the direction of its long axis, such that the length of the positioning arm can be increased or decreased. In some embodiments, the telescoping motion of the connecting arm is controlled by rotation of a dial situated at its second end. In certain embodiments, the telescoping motion of the positioning arm is controlled by rotation of a dial situated at its first end. In certain embodiments, the medical instrument is selected from the group consisting of: a cannula, a biopsy needle, a needle, a tube, a cauterization device, a laser, a drill, an endoscope, a guidewire, a fiberoptic device, an electrode, a saw, an ultrasonic device, a spectroscopic device, a camera, an electrical sensor, a thermal sensor, a catheter, a draining tube, and combinations thereof. In some embodiments, the apparatus further includes a side clamp attached to the securing arm, wherein the side clamp is configured to attach to an elongated object. In some embodiments, the securing arm is removably attached to the connecting arm. In various embodiments, the positioning arm is removably attached to the connecting arm and/or the guiding arm. In some embodiments, the side clamp is removably attached to the securing arm. In certain embodiments, the elongated object is a device selected from the group consisting of: a liquid reservoir, a gas reservoir, a pump, an imaging device, and combinations thereof.

In various embodiments, the invention teaches a system. In some embodiments, the system includes any apparatus described above and a tissue retractor attached to the securing arm of the apparatus by one or more clamps of the securing arm. In some embodiments, the system further includes an instrument attached to the instrument attaching component, wherein the instrument is selected from the group consisting of: a cannula, a biopsy needle, a needle, a tube, a cauterization device, a laser, a drill, an endoscope, a guidewire, a fiberoptic device, an electrode, a saw, an ultrasonic device, a spectroscopic device, a camera, an electrical sensor, a thermal sensor, a catheter, a draining tube, and combinations thereof. In some embodiments, the instrument includes a cannula with a needle situated at the end thereof. In some embodiments, the cannula and needle are configured to inject cells into a region of interest in a subject's body. In various embodiments, the cannula contains a quantity of neural progenitor cells. In some embodiments, the neural progenitor cells express glial cell line derived neurotrophic factor. In certain embodiments, the region of interest is the subject's spine. In some embodiments, the system further includes a liquid reservoir and a pump connected thereto, wherein the liquid reservoir and pump are attached to the side clamp.

In various embodiments, the invention teaches a method for performing a surgical procedure on a subject. In some embodiments, the method includes attaching any apparatus described herein above to an arm of a tissue retractor that is engaged in an incision in the subject's body, and guiding a medical instrument attached to the guiding arm of the apparatus through the incision in the subject's body. In certain embodiments, the medical instrument is a cannula with a needle situated at the end thereof. In some embodiments, the cannula and needle are configured to inject cells into a region of interest in the subject's body. In some embodiments, the region of interest is the subject's spine. In some embodiments, the cells are neural progenitor cells. In some embodiments, the subject has been diagnosed with amyotrophic lateral sclerosis (ALS). In various embodiments, the method further includes performing imaging of the region of interest in the subject's body. In some embodiments, the imaging performed is selected from the group consisting of computed tomography (CT), magnetic resonance imaging (MRI), ultrasound, and combinations thereof. In some embodiments, the method further includes injecting neural progenitor cells expressing glial cell line derived neurotrophic factor into the subject's spine.

BRIEF DESCRIPTION OF THE DRAWINGS

Exemplary embodiments are illustrated in the referenced figures. It is intended that the embodiments and figures disclosed herein are to be considered illustrative rather than restrictive.

FIG. 10 also shows rotating dial 101 causes motion of instrument attachment component 107 along the z-axis.

DETAILED DESCRIPTION OF THE INVENTION

Figure 1A:
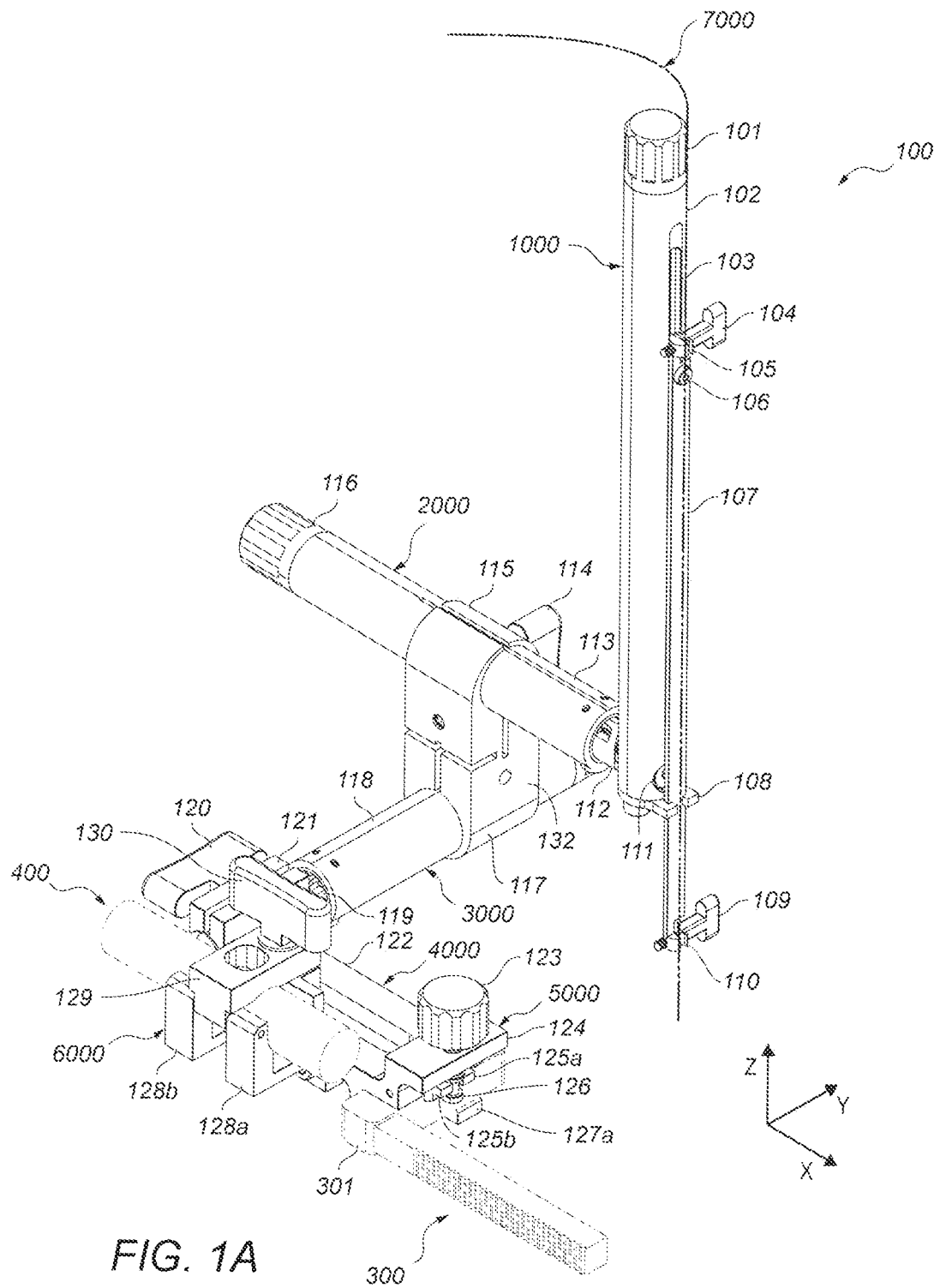
FIG. 1A depicts, in accordance with an embodiment of the invention, stereotactic apparatus 100. Stereotactic apparatus 100 is clamped to arm 301 of tissue retractor 300. Cylindrical object 400 is fastened to stereotactic apparatus 100 by side clamp 6000.
Figure 1B:
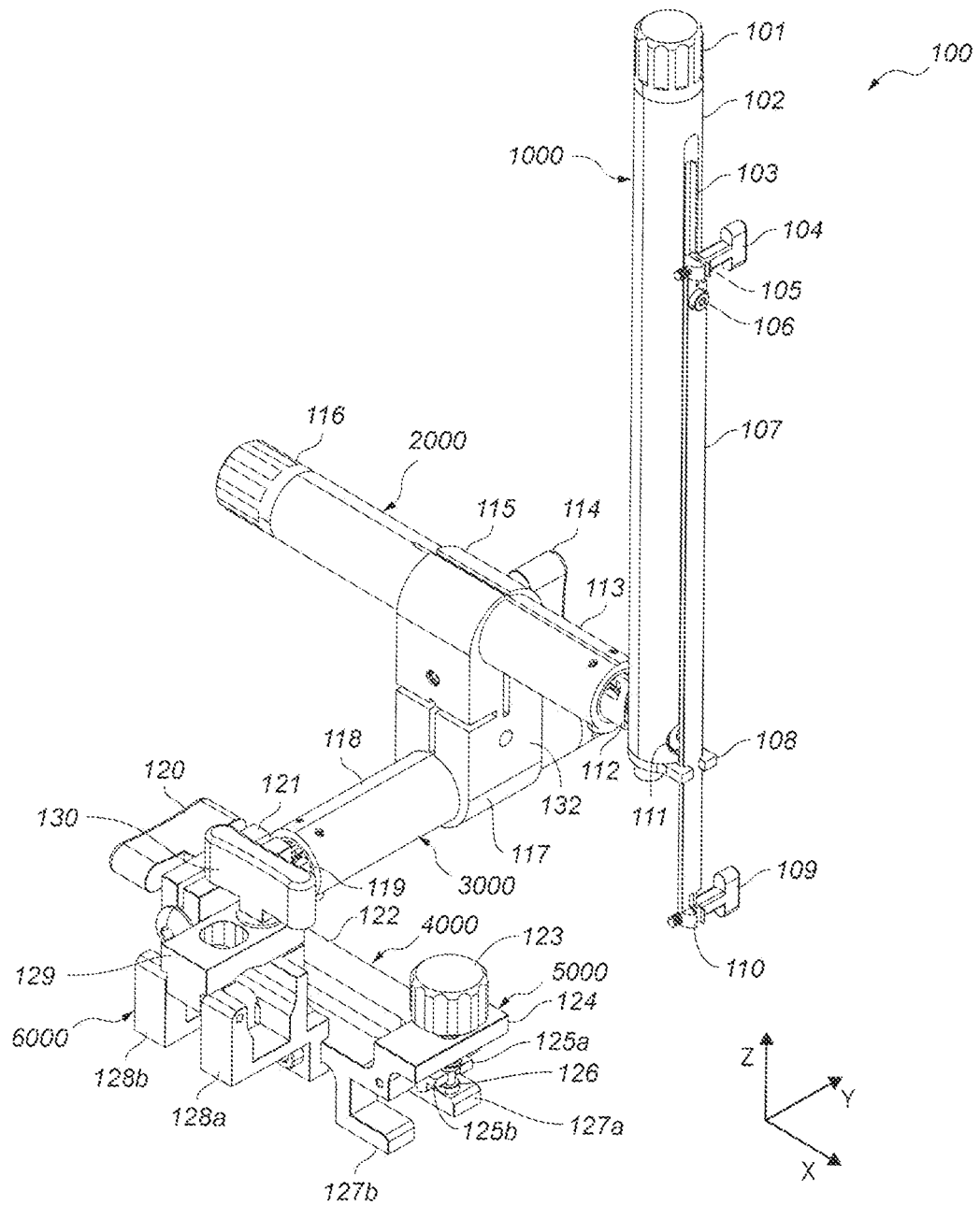
FIG. 1B depicts stereotactic apparatus 100 without attachment to a tissue retractor.

All references cited herein are incorporated by reference in their entirety as though fully set forth. Unless defined otherwise, technical and scientific terms used herein have the same meaning as commonly understood by one of ordinary skill in the art to which this invention belongs. *Szycher's Dictionary of Medical Devices* CRC Press, 1995, may provide useful guidance to many of the terms and phrases used herein. One skilled in the art will recognize many methods and materials similar or equivalent to those described herein, which could be used in the practice of the present invention. Indeed, the present invention is in no way limited to the methods and materials specifically described.

In some embodiments, properties such as dimensions, shapes, relative positions, and so forth, used to describe and claim certain embodiments of the invention are to be understood as being modified by the term "about."

With the aforementioned shortcomings of previously existing technologies in mind, the inventors developed novel stabilizing apparatuses and methods of use thereof. While one of skill in the art would readily appreciate that there are many possible applications of the apparatuses described herein, certain embodiments are especially useful for procedures performed on or around the spinal cord, including delivery of cutting edge cellular and molecular therapies thereto. Importantly, all versions of the devices described herein also render the use of percutaneous posts unnecessary and therefore allow for a minimally invasive surgical approach.

Although numerous embodiments of stereotactic apparatuses are described herein, there are certain features common to all of them. First, each apparatus includes one or more components that make up a "securing section" capable of stably connecting to an arm of a tissue retracting device. The second feature common to each of the apparatuses described herein is a "positioning section," which includes one or more components capable of positioning an instrument over a desired location in a subject's body. The third common feature is a "connecting section," which serves to operably connect the positioning section and the securing section. A fourth common feature is a "guiding section," which can be used to guide an instrument into or remove an instrument from a subject's body.

Provided below are descriptions of various components, combinations of components, and configurations of components relative to one another that can be used to arrive at each of the common sections described above. Additional features that can be added to the stereotactic apparatus are also described.

Securing Section

In some embodiments, the securing section of the stereotactic apparatus is configured to removably attach to an arm of a tissue retractor. Removable attachment can be accomplished in any of a number of ways, using a wide range of components and combinations thereof. Merely by way of non-limiting examples, the securing section could attach to the arm of a tissue retractor by using one or more clasps, one or more clamps, one or more magnets, one or more screws, one or more pins, one or more slot and groove arrangements, one or more straps, combinations thereof and the like. Therefore, each of these components, and modified versions thereof, are within the scope of the invention. It is further contemplated that the attaching portion of the apparatus could be configured to attach to any of a variety of types of equipment that might be found in a setting in which a medical procedure is performed, including, but in no way limited to a table, a lamp, a brace, a tray, imaging equipment, and the like. It is also contemplated that the device could be configured for use in a non-surgical setting, in which it may be used to perform any objective that requires the use of precision guidance. It is also contemplated that the device could be scaled appropriately for such objectives.

Figure 3:
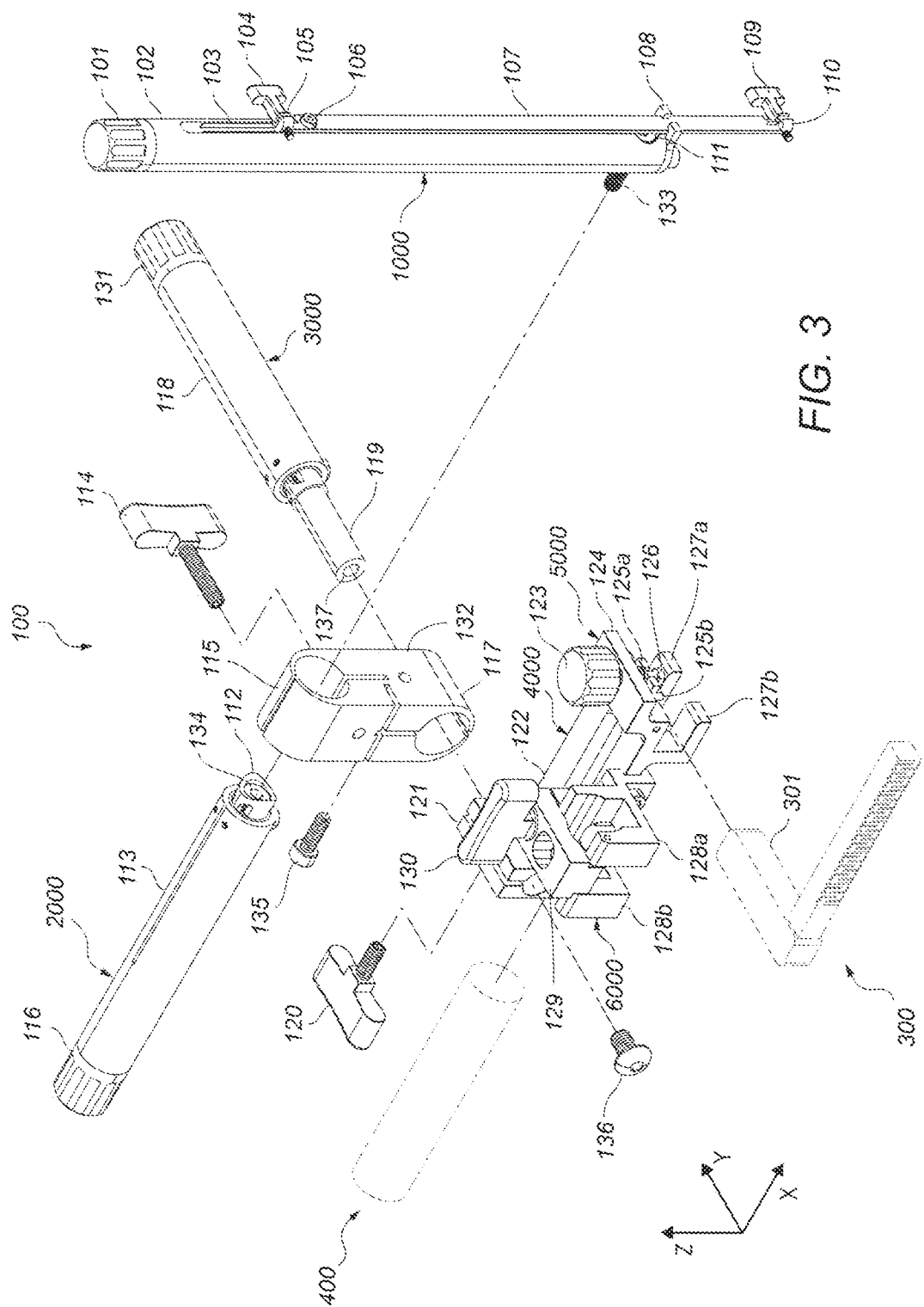
FIG. 3 depicts, in accordance with an embodiment of the invention, a partially exploded view of stereotactic apparatus 100.

In some embodiments, a clamping mechanism is incorporated on the securing arm, and used to attach the stereotactic apparatus to the arm of a tissue retractor. One of skill in the art would readily appreciate that numerous types of clamping mechanisms are suitable to accomplish this function. One non-limiting example is depicted in FIG. 3, which shows clamping mechanism 5000 of securing arm 4000 can be used to clamp arm 301 of tissue retractor 300 (partially shown). A more detailed view of the clamping components of this particular embodiment is shown in FIG. 21, and the individual components (and their functions) are thoroughly described in the examples section.

Figure 21:
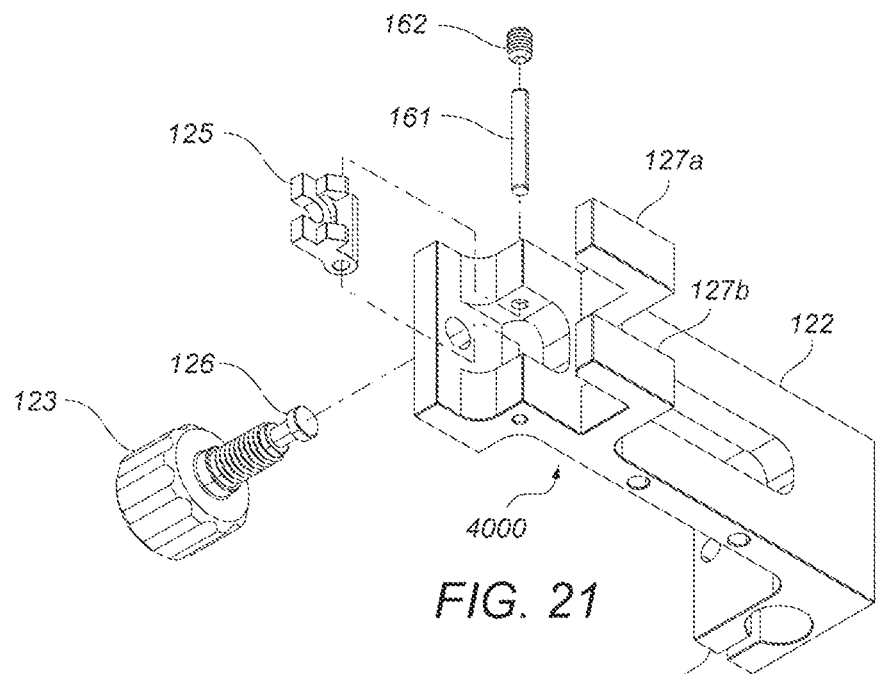
FIG. 21 depicts, in accordance with an embodiment of the invention, an alternate exploded view of securing arm 4000.

Importantly, the clamping mechanism shown in FIG. 21 can be used to securely and removably attach a stereotactic apparatus (including stereotactic apparatus 100) to the arm of a number of different types of tissue retractors. Non-limiting examples of retractors to which the clamping mechanism can attach include the Mast Quadrant Retractor System (Medtronic), the MARS Retractor System (Globus Medical), the Spyder Retractor System (Aesculap), the Ravine Retractor System (K2M), the Synframe Retractor System (DePuy Synthes), and the Luxor Retractor System (Stryker). One of skill in the art would readily appreciate that any retractor with one or more arms similar to those retractors described above could also be used in conjunction with the inventive stereotactic apparatuses described herein. One of skill in the art would further appreciate that the alternative attaching mechanisms described above would allow for the attachment of the securing section of an apparatus to one or more arms of alternative retractor devices that are not specifically listed above.

Positioning Section

Figure 15:
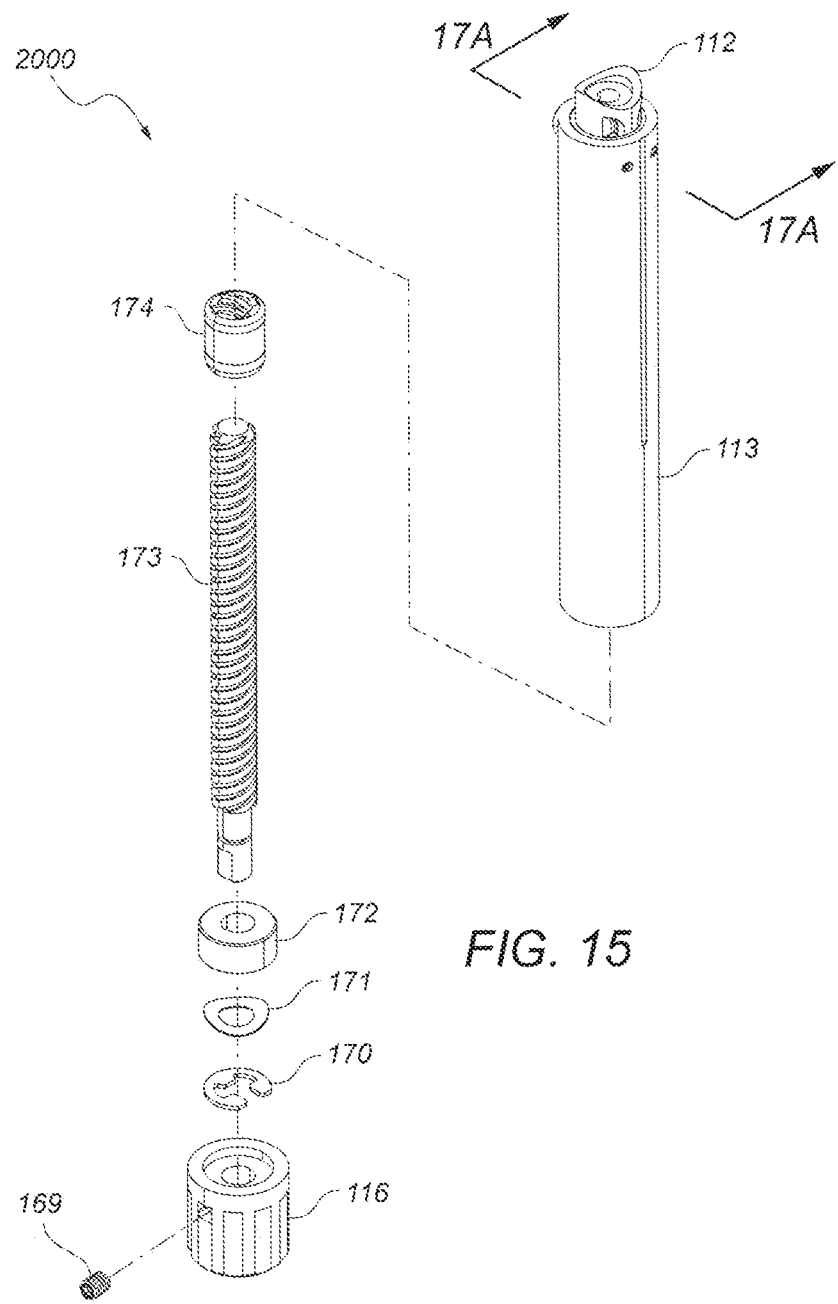
FIG. 15 depicts, in accordance with an embodiment of the invention, a partially exploded view of positioning arm 2000. Arrows labeled "17A" indicate the cross section represented in FIG. 17A.
Figure 16:
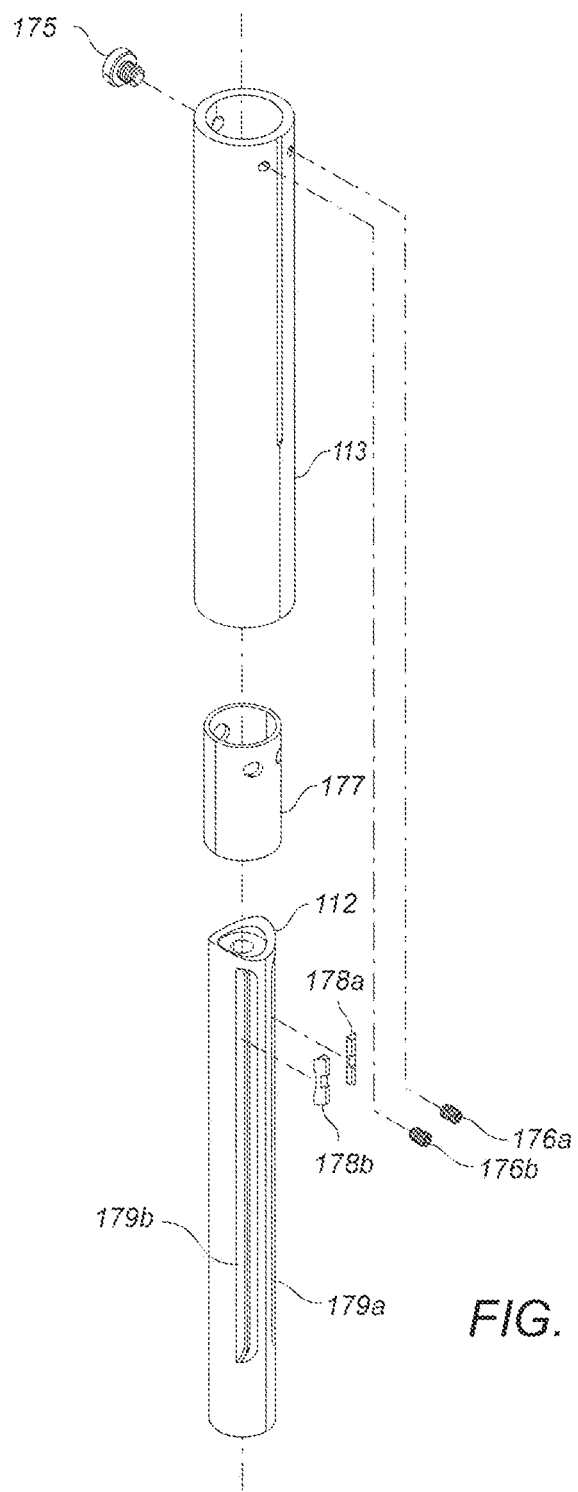
FIG. 16 depicts, in accordance with an embodiment of the invention, a partially exploded view of a portion of positioning arm 2000.

The purpose of the positioning section is to allow for stable positioning of an instrument over a desired anatomical location, by positioning a guiding arm to which the instrument is attached. One of skill in the art would readily appreciate that there are many possible components and configurations thereof that could make up a positioning section of the stereotactic apparatus. In certain embodiments the positioning section includes components that allow for telescoping motion, which permits fine adjustment of the position of the instrument attached to the guiding arm. In some embodiments, a positioning arm is used. In various embodiments, the positioning arm includes two or more nested elements that are operably connected to one another as well as an input component (e.g., a dial) in a manner that allows for telescoping motion. In a non-limiting example, the telescoping motion is accomplished by the components depicted in FIGS. 15-17. The interaction between and operation of the components of FIGS. 15-17 are thoroughly described in the examples section.

One of skill in the art would readily appreciate that there are numerous possible ways of stabilizing and controlling the telescoping motion of the positioning arm. Merely by way of non-limiting example, if a mechanism with a threaded shaft is used, as depicted in FIGS. 15-17, the number of threadings on the shaft and the pitch of the threadings can be used to dictate the degree to which the positioning arm telescopes in response to associated input (e.g. rotation of a dial). In certain embodiments, the positioning arm is stabilized through the use of components that limit its range of motion in all but the axis along which it is advanced or retracted. Merely by way of non-limiting example, FIG. 16 shows the configuration of guiding set screws 176a and 176b and supporting elements 178a and 178b is used to apply pressure on L-shaped tracks 179a and 179b of inner nested element 112 of positioning arm 2000. FIG. 16 also shows that screw 175 is positioned on the opposite side of set screws 176a and 176b, in order to add to the stability of inner nested component 112, especially while it is being extended or retracted.

One of skill in the art would readily appreciate that there are many possible ways of attaching the positioning arm to the guiding arm. As shown in FIG. 3, one way positioning arm 2000 can be connected to guiding arm 1000 is through the use of screw 133 that traverses the short axis of guiding arm 1000 and connects to grooved receiving socket 134.

Connecting Section

Figure 12:
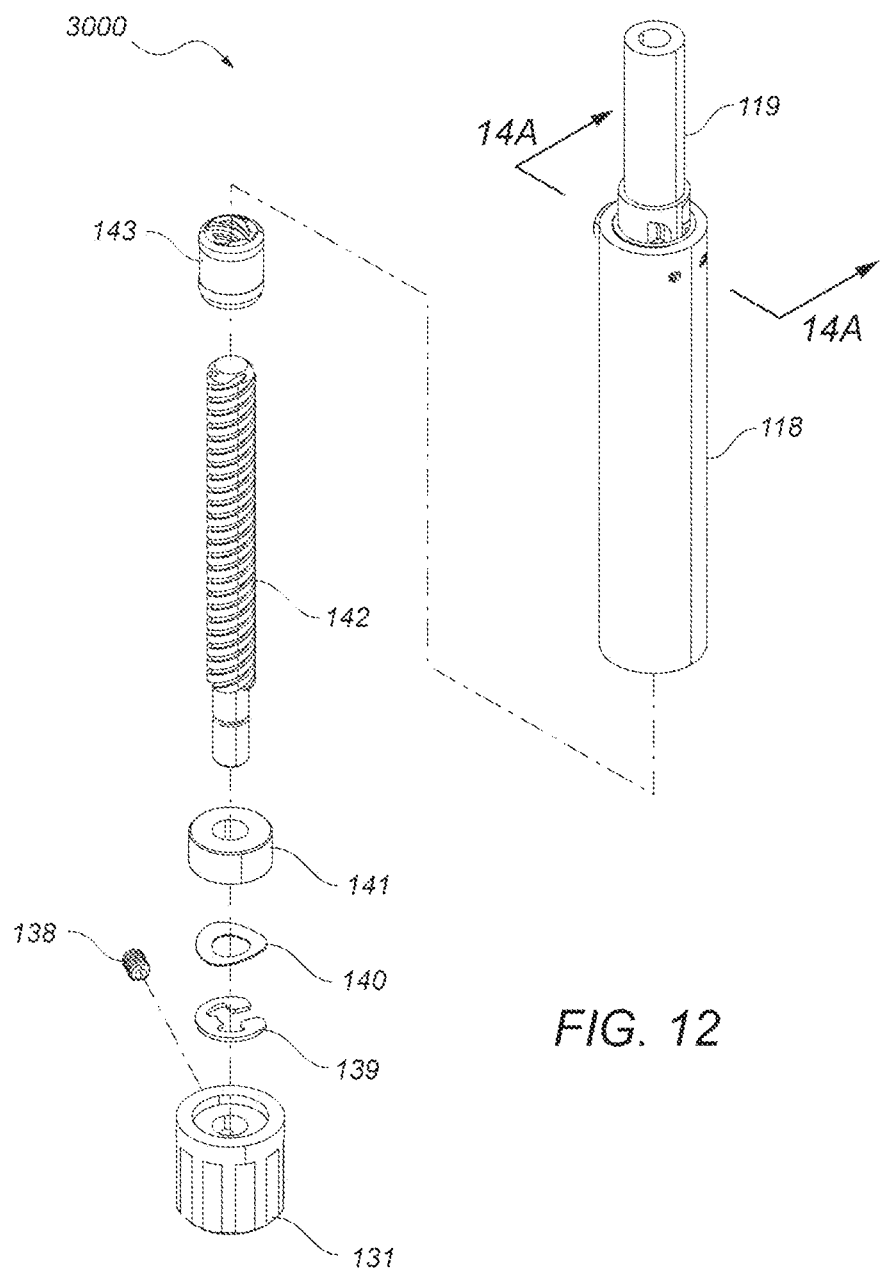
FIG. 12 depicts, in accordance with an embodiment of the invention, a partially exploded view of connecting arm 3000. Arrows labeled "14A" indicate the cross section represented in FIG. 14A.

The long axis of the connecting section of the stereotactic apparatus can be configured to be perpendicular to the long axis of the securing section and the positioning section. In some embodiments, the connecting section, like the positioning section, is a telescoping arm. In some embodiments, the telescoping connecting arm can be stabilized and controlled by any of the aforementioned components associated with the positioning section. Merely by way of non-limiting example, telescoping of the connecting arm can be accomplished through the use of the components shown in FIGS. 12-14, the interaction between which and function of which are thoroughly described in the examples section.

Guiding Section

The guiding section can be configured to allow for the attachment of one or more instruments that can be extended into and retracted from a subject's body. In some embodiments, the guiding section includes a guiding arm. There are many possible ways by which an instrument can be attached to a guiding arm. One of skill in the art would readily appreciate that the possible components that could be used to attach an instrument to a guiding arm would vary depending upon the dimensions and nature of the instrument to be attached. Merely by way of non-limiting examples, attachment of various instruments to the guiding arm can be accomplished by using one or more straps, clamps, clasps, magnets, and combinations thereof.

Examples of instruments that could be attached to the guiding arm include, but are in no way limited to a cannula, a biopsy needle, a needle, a tube, a cauterization device, a laser, a drill, an endoscope, a guidewire, a fiberoptic device, an electrode, a saw, an ultrasonic device, a spectroscopic device, a camera, an electrical sensor, a thermal sensor, a catheter, a draining tube, an imaging device (such as any of those listed and/or described herein) and the like. In certain embodiments, the instrument guided by the inventive apparatuses described herein includes a guide needle and an injection needle configured to be concentrically housed therein. In some embodiments, the concentric arrangement of the guide needle and the injection needle allows the injection needle to be advanced through the guide needle, once the guide needle is properly positioned in a subject during a medical procedure, so that the injection needle can deliver a payload of biological or chemical material to an appropriate site in the subject. In some embodiments, the instrument guided and/or stabilized by the inventive apparatus is the spinal multisegmental cell and drug delivery device described in U.S. patent application Ser. No. 12/598,667, which is incorporated by reference herein in its entirety as though fully set forth.

Figure 18:
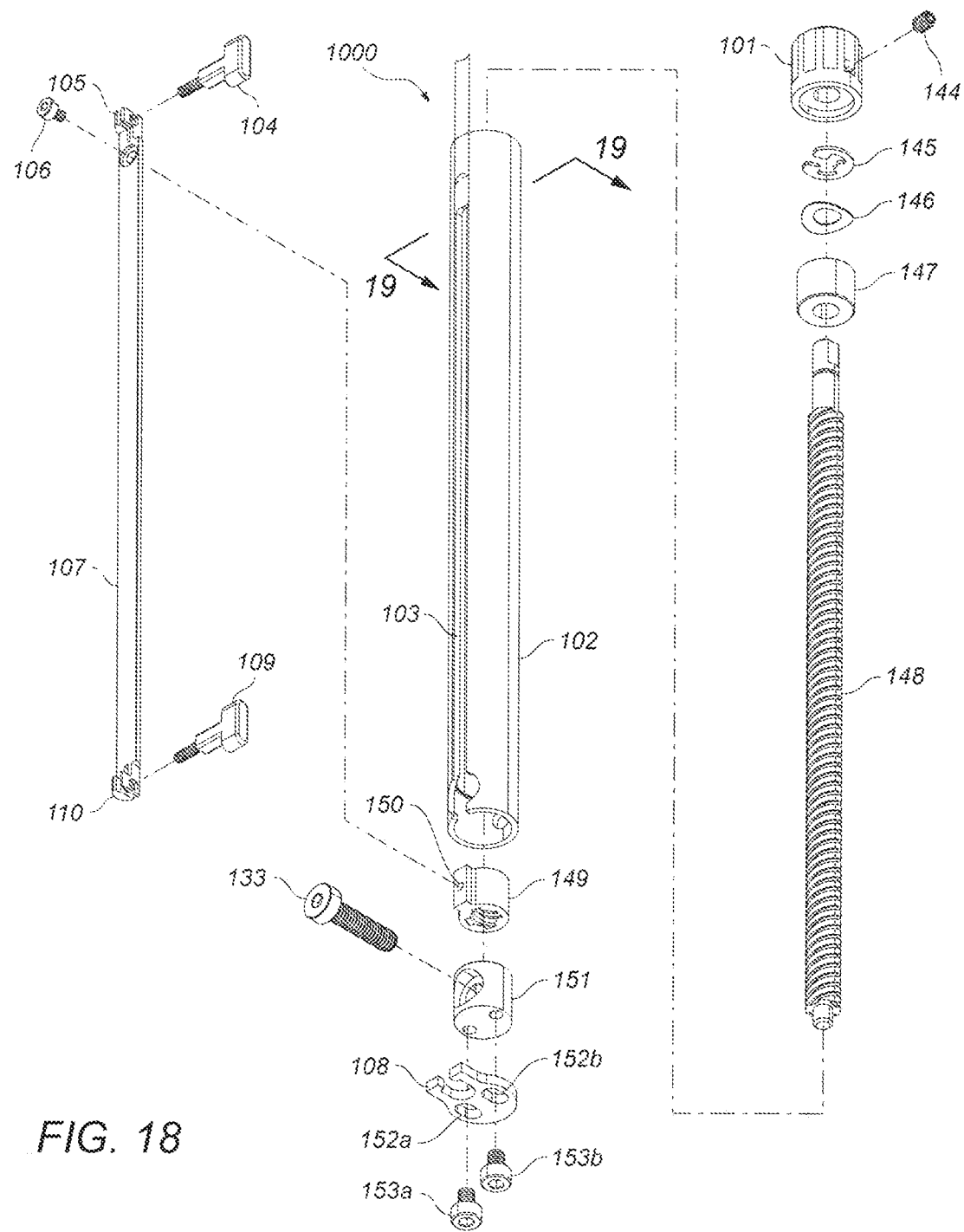
FIG. 18 depicts, in accordance with an embodiment of the invention, an exploded view of guiding arm 1000. Arrows labeled "19" indicate the cross section represented in FIG. 19.
Figure 19:
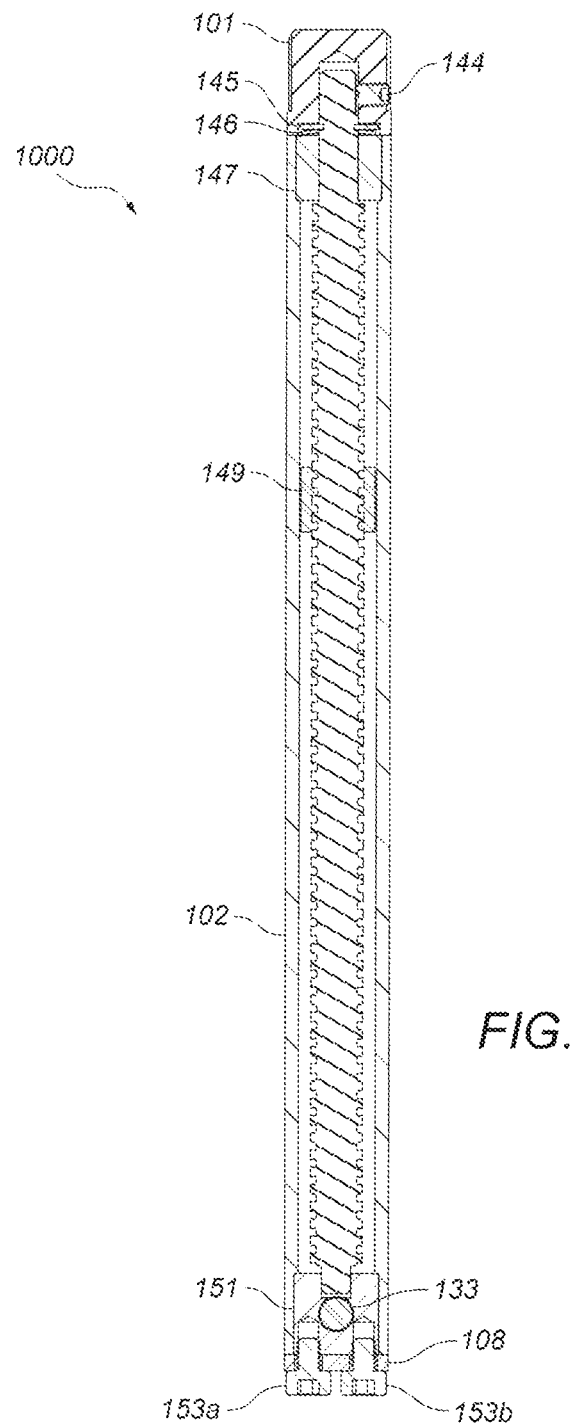
FIG. 19 depicts, in accordance with an embodiment of the invention, a cross-sectional view of the long axis of guiding arm 1000.
Figure 20:
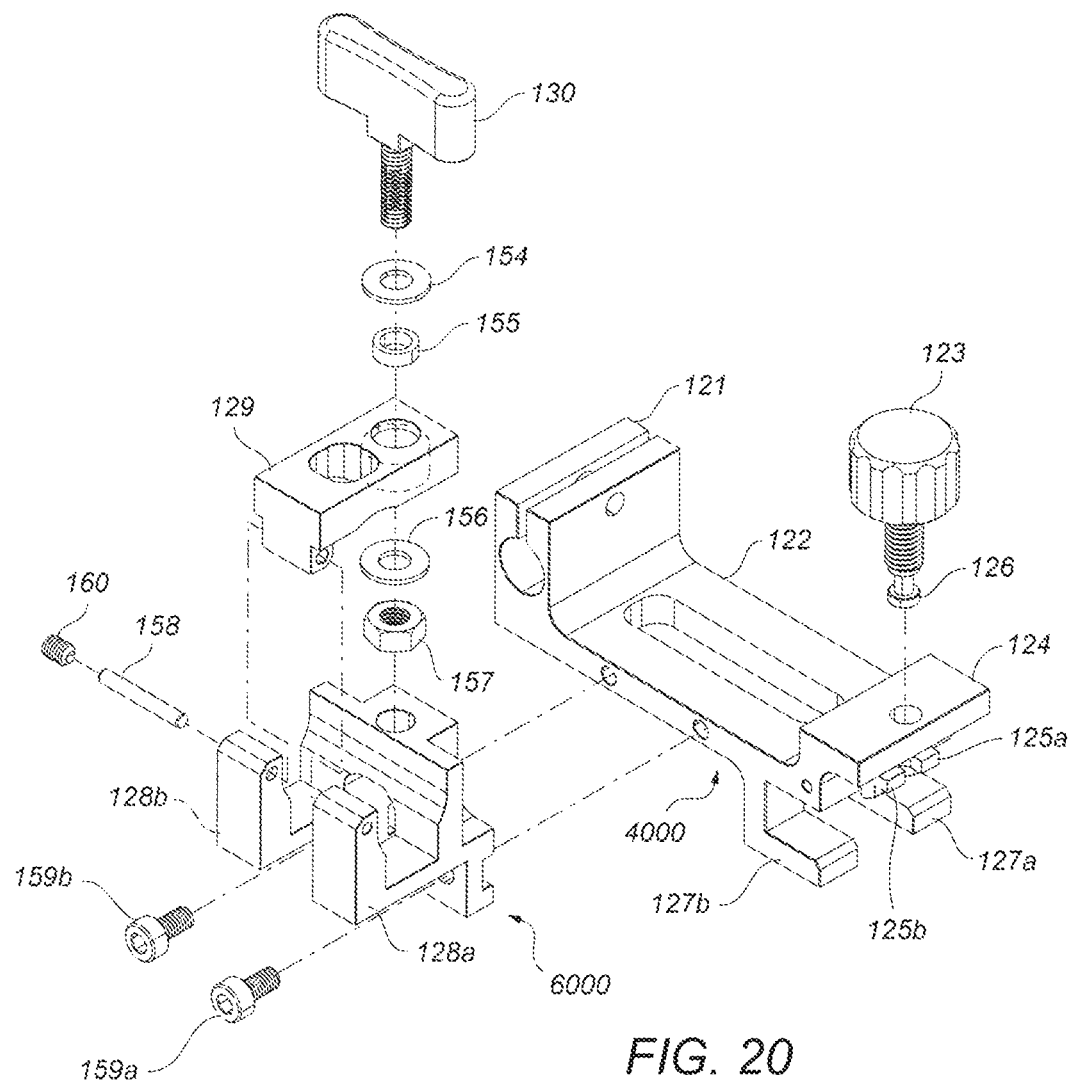
FIG. 20 depicts, in accordance with an embodiment of the invention, an exploded view of side clamp 6000, and it's attachment to securing arm 4000.

One of skill the art would also readily appreciate that there are numerous possible ways by which the apparatus can be configured to allow for an instrument to be extended into and retract from a subject while connected to the guiding arm. FIG. 18 depicts one non-limiting example of a mechanism that can be used for that purpose. The association between the components shown in FIG. 18 and the function of those components are thoroughly described in the examples section.

Orientation of Individual Sections

Figure 5:
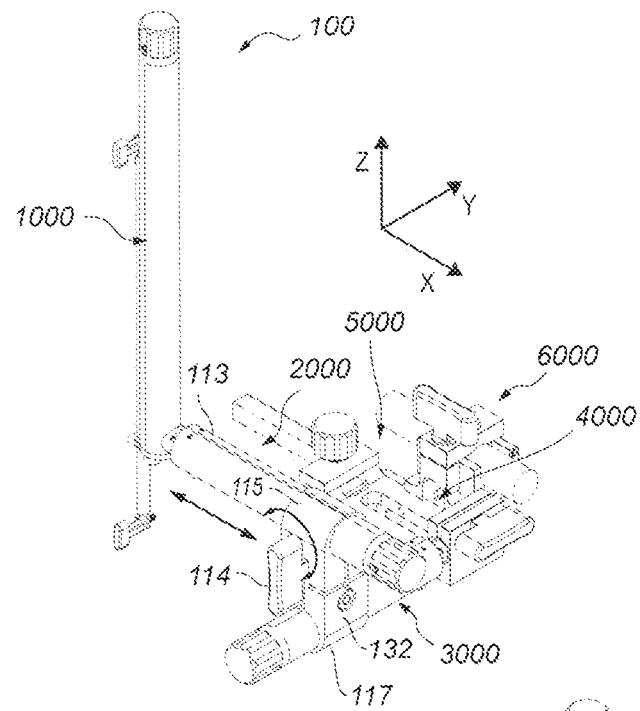
FIG. 5 depicts, in accordance with an embodiment of the invention, loosening knob 114 allows for adjustment of the position of positioning arm 2000 along the x-axis.
Figure 8:
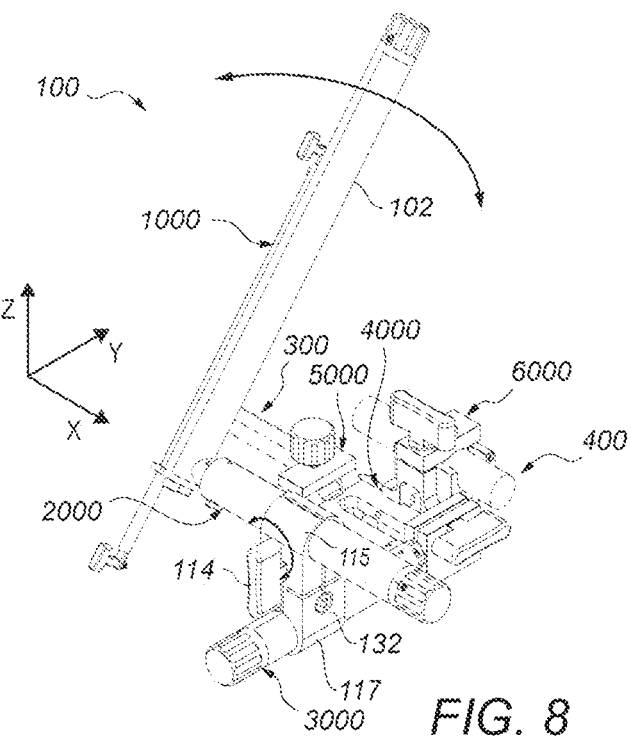
FIG. 8 depicts, in accordance with an embodiment of the invention, loosening of knob 114 allows for rotation of positioning arm 2000 around the x-axis and associated motion of guiding arm 1000 along the y-z plane.

The securing section, connecting section, positioning section and guiding section can be connected to one another by any of a variety of ways depending upon the desired range of motion of each section. In some embodiments, a perpendicular orientation of the positioning arm and connecting arm, relative to one another, is established through the use of a component with perpendicularly situated clamping collars. In an embodiment, cross clamp 132 (depicted in FIG. 1A) can be used. As shown in FIG. 5, when cross clamp 132 is used to secure positioning arm 2000, knob 114 can be rotated to loosen collar 115, thereby allowing for adjustment of the position of positioning arm 2000 along the x-axis. As shown in FIG. 8, loosening of collar 115 by rotating knob 114 also allows for rotation of positioning arm 2000 along the x-axis, which translates into motion of guiding arm 1000 along the y-z plane.

Figure 6:
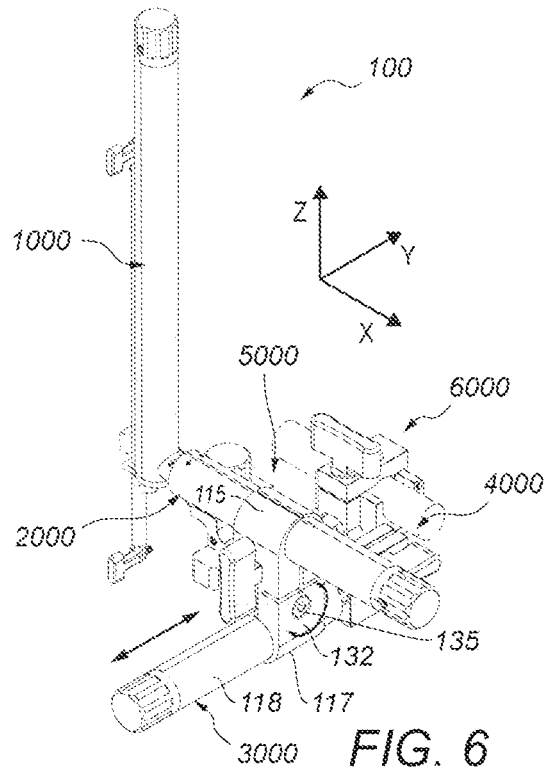
FIG. 6 depicts, in accordance with an embodiment of the invention, loosening screw 135 allows for adjustment of the position of positioning arm 2000 along the y-axis.
Figure 9:
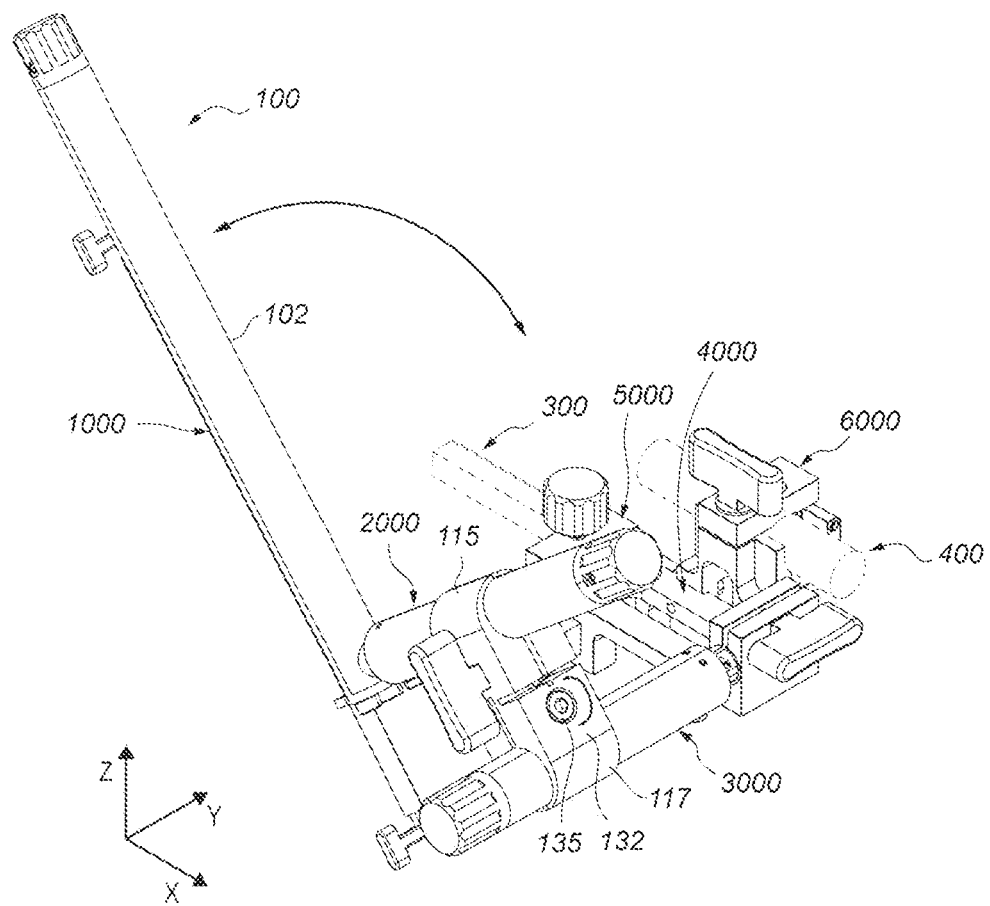
FIG. 9 depicts, in accordance with an embodiment of the invention, loosening screw 135 allows for rotation of cross clamp 132 around the y-axis, and associated motion of guiding arm 1000 along the x-z plane.

As shown in FIG. 6, when cross clamp 132 is used to secure connecting arm 3000, rotation of screw 135 loosens lower collar 117, which allows for adjustment of the position of positioning arm 2000 along the y-axis. As shown in FIG. 9, loosening collar 117 also allows for rotation of cross clamp 132 along the y-axis, which in turn translates into motion of guiding arm 1000 along the x-z plane.

Additional Features

The main sections of the stereotactic apparatuses described above can be configured to allow for incorporating additional features on the apparatuses. For example, the stereotactic apparatus can include clamps (or any other means of attachment described herein) situated on one or more of the main sections of the apparatus (i.e. guiding section, positioning section, connecting section, and attaching section) for attaching additional useful instruments or devices.

Figure 22:
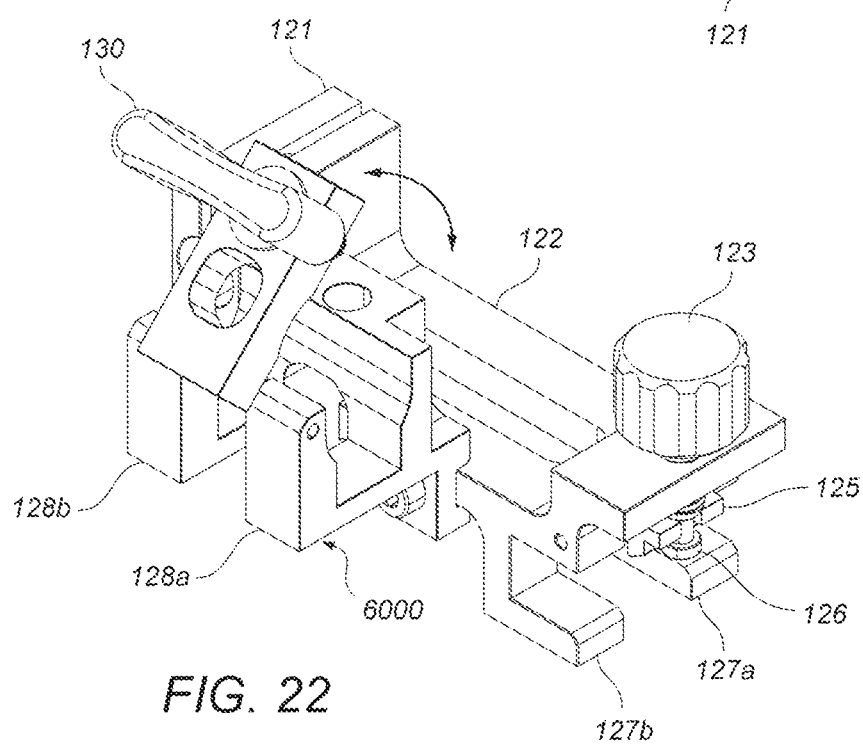
FIG. 22 depicts, in accordance with an embodiment of the invention, side clamp 6000.
Figure 23:
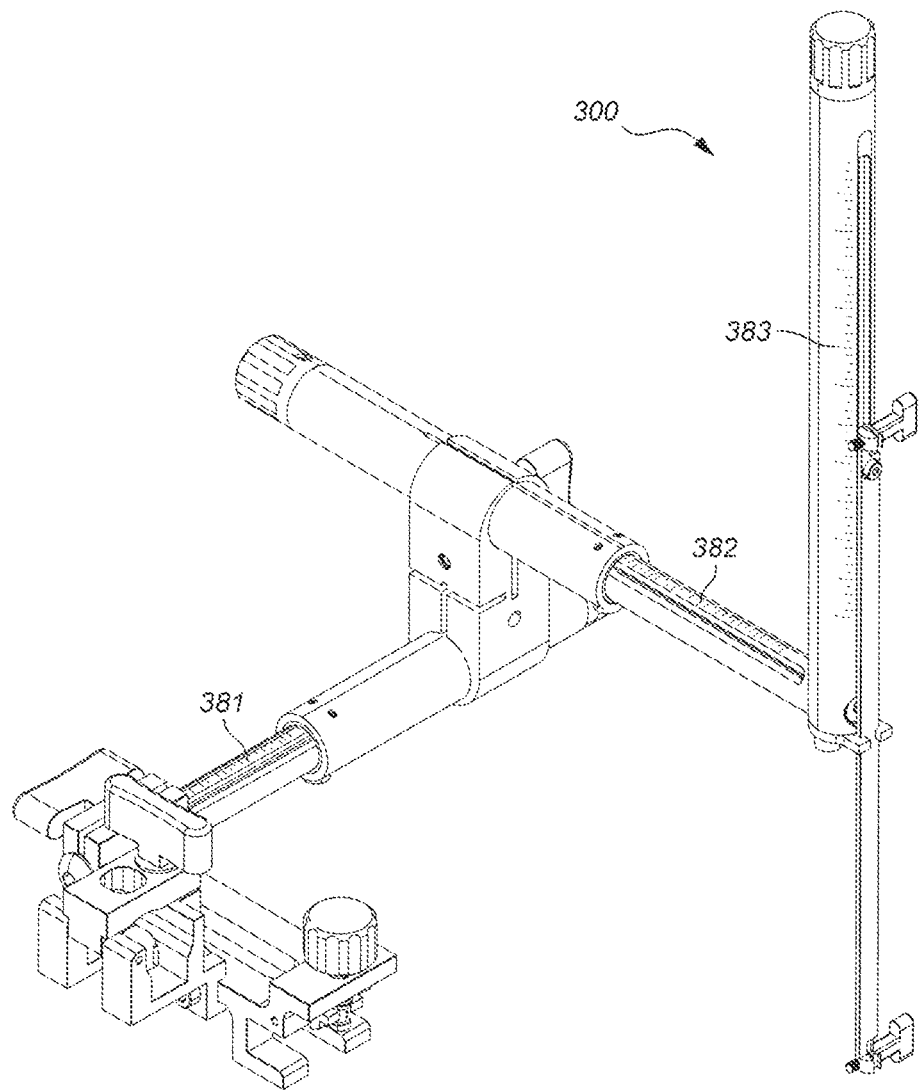
FIG. 23 depicts, in accordance with an embodiment of the invention, scales 381, 382, and 383 on device 300. Device 300 is identical to device 100 with respect to all other features.

In certain embodiments, the stereotactic apparatus includes a side clamp attached to the securing section, which allows for attaching a useful instrument or device. For example, as demonstrated in FIG. 3, side clamp 6000 can be used to hold cylindrical device 400. The components of side clamp 6000 are clearly shown in FIG. 22, and thoroughly described in the examples section. One of skill in the art would readily appreciate that a side clamp such as side clamp 6000 can be used to attach any of a number of devices with appropriate dimensions to the stereotactic apparatus.

Devices that can be attached to the stereotactic apparatuses described herein can include, but are in no way limited to, a pump, a reservoir for containing a substance to be injected into a subject's body, a reservoir for receiving a substance removed from a subject's body, a small motor, a control panel, an imaging device or portion thereof (including any appropriately sized imaging device described herein) and the like. In some embodiments, the device attached is a fiber optic camera that can be positioned to view an opening in a patient's body in which a tissue retractor is engaged. In some embodiments, a reservoir attached to the apparatus can be configured to hold any of a variety of useful substances, including but in no way limited to cells, gasses, liquids, medications, contrast agents, radioactive materials, combinations thereof, and the like.

An additional category of devices that could be attached to one or more sections of the inventive apparatuses described herein is a light source. In various embodiments, the inventive apparatuses may include one or more light sources configured to project light onto a region of interest on or in a subject's body during a medical procedure. In some embodiments, one or more of the light sources is attached to the guiding arm. In some embodiments, the light source is a laser. In some embodiments, the light source is a relatively high energy laser that can be used for cauterizing or cutting. In some embodiments, the light source is a relatively low energy laser that can be used for visually targeting a region on or in a subject's body for incision or other medical intervention. In other embodiments, the light source provides relatively low energy light for aiding in visualizing a region of interest. In still other embodiments, the light source provides light of a wavelength that causes fluorescence of a fluorophore. In various embodiments, the fluorophore is introduced into a subject's body directly, present in cells residing in a subject's body, or naturally occurring. Merely by way of non-limiting examples, the wavelength of the light projected by the light source can be in the visible, IR, or UV range.

Another category of devices that can be incorporated onto the stereotactic apparatuses described herein is an imaging modality. In some embodiments, the imaging modality is attached to the guiding arm. However, one of skill in the art would recognize that all or a portion of an imaging modality (or any other device described herein, or similar thereto) of an appropriate size could be attached to any arm of the apparatuses described herein, by any form of attachment described herein. In some embodiments, the imaging modality includes a device used to perform MRI, CT, or ultrasound imaging. In some embodiments, an endoscope is attached to the guiding arm. In some embodiments, one or more components of a microscope or other magnifying instrument are attached to the guiding arm. One of skill in the art would readily appreciate that any of a number of other useful instruments of a size suitable for attaching to the guiding arm could be used in conjunction with the inventive apparatuses described herein, and attached thereto by any means for attachment described herein.

As indicated above, in some embodiments, the apparatus is configured so that the positions of the various sections described above can be manipulated manually. However, one of skill in the art would readily appreciate that the apparatus could also be configured with one or more motors, gears, pulleys, and electronic controls, so that one or more sections of the apparatus could be electronically controlled.

In some embodiments, the apparatuses described herein are made of stainless steel. In some embodiments, the apparatuses are made of titanium, austenitic steel, martensitic steel, brass, carbon fiber, plastic, combinations thereof, and the like. In preferred embodiments, the material or materials used are biocompatible.

In some embodiments, the invention teaches a method that includes using any of the stereotactic apparatuses described herein for the purposes of facilitating one or more of the processes of (1) introducing a substance into a subject, (2) removing a substance from a subject, and (3) manipulating a portion of a subject's body. One of skill in the art would readily appreciate that the device could be used to introduce a substance into and/or remove a substance from any portion of subject's body, including, but in no way limited to an organ, joint (shoulder, hip, knee, etc.), ligament, tendon, muscle, eye, cavity, or any other tissue. In some embodiments, the substances introduced into the subject's body can include but are in no way limited to biological and/or synthetic substances. Biological substances can include, but are in no way limited to stem cells, neural progenitor cells, tissues, blood, hormones, clotting factors, vectors (including but not limited to viral vectors, plasmids and the like), DNA, RNA, proteins, growth factors, inhibitory substances, matrices, combinations thereof, and the like. Synthetic substances that can be introduced into a subject's body can include but are in no way limited to pharmaceutical agents, markers (including but not limited to biomarkers or any other type of marker that could be visualized with or without the use of imaging equipment), implantable medical devices, electrical sensors, electrical stimulators, glue, sutures, chemotherapeutics, radioactive substances, hyperpolarized substances, combinations thereof, and the like.

Substances that can be removed from a subject's body utilizing the inventive apparatuses and methods include, but are in no way limited to, any of the above-named substances that can be introduced into a subject, in addition to tissues, organs, cancer cells and pre-cancer cells, bone marrow, fluid, foreign bodies, combinations thereof, and the like.

In some embodiments, the inventive method includes using any of the inventive apparatuses described herein to position any of the instruments described herein such that they can be introduced between the spreading elements of a retractor device described herein and then the adjacent sections of tissue associated therewith. In an embodiment, the inventive method includes using guiding arm 1000 of inventive apparatus 100 to introduce a needle associated with a cannula into any portion of a subject's spinal cord (including the section specifically described in the non-limiting examples herein). A payload of neural progenitor cells is then advanced through the cannula and needle and into the subject's spinal cord.

In some embodiments, the invention teaches a method that includes (1) attaching any apparatus described herein to the arm of a retractor, (2) attaching any instrument described herein to the guiding arm of the apparatus (by any means described above), and (3) advancing the instrument through the separating elements of the retractor and into a subject's body through an incision in the subject's body. FIG. 1D shows a non-limiting example of how the components of an apparatus can be situated to perform this method.

EXAMPLES

Example 1

Stereotactic Apparatus with Side Clamp

Figure 10:
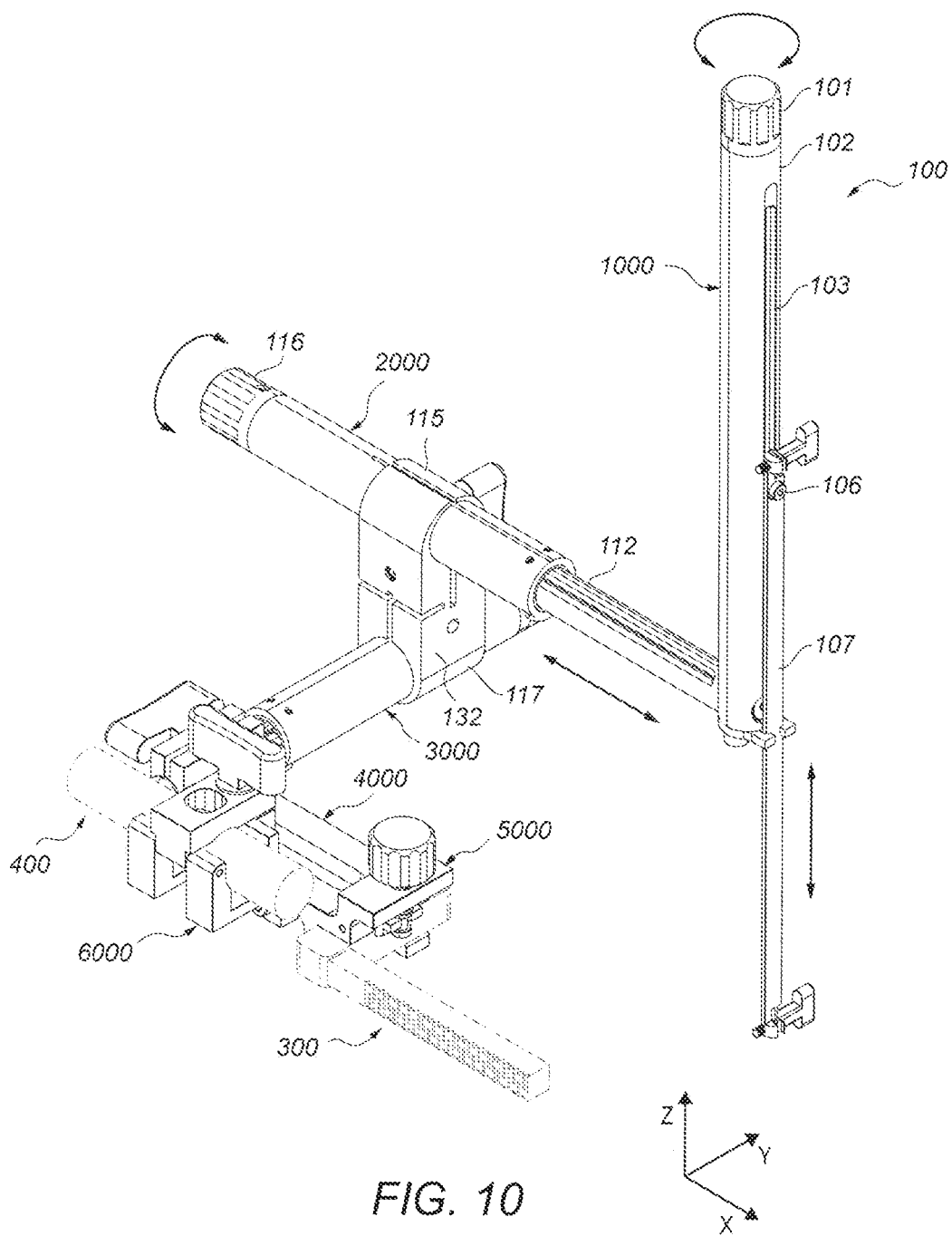
FIG. 10 depicts, in accordance with an embodiment of the invention, rotating dial 116 causes telescoping of inner nesting element 112 of positioning arm 2000.

FIG. 1A depicts exemplary stereotactic apparatus 100. Stereotactic apparatus 100 includes guiding arm 1000, which includes an elongated channel 103 situated along its long axis (FIG. 1A). Guiding arm 1000 includes a dial 101 and an elongated cylindrical body 102 (FIG. 1A). Guiding arm 1000 also includes instrument attachment component 107, and clamps 105 and 110 which are tightened and loosened by screws 104 and 109, respectively (FIG. 1A). The guiding arm 1000 further includes instrument attachment component guide 108. FIG. 18 depicts an exploded view of guiding arm 1000, in which the assembly of threaded shaft 148, bushing 147, curved spring washer 146, radial ring 145, set screw 144, and dial 101 is shown. FIG. 18 also depicts the assembly of screws 153a and 153b, instrument attachment component guide 108 (with screw receiving holes 152a and 152b), cylindrical receiving stopper 151, and screw 133. FIG. 18 shows instrument attachment component 107 is attached to sliding carriage 149 through hole 150. FIGS. 10 and 18 show that as dial 101 is turned, intermediate components 145-148 (shown in FIG. 18) cause carriage component 149 to glide along elongated channel 103 (along the z-xis), together with instrument attachment component 107. It follows that any instrument attached to instrument attachment component 107 would also travel along the z-axis when the position of instrument attachment component 107 is adjusted by rotating dial 101.

Figures 17A, 17B:
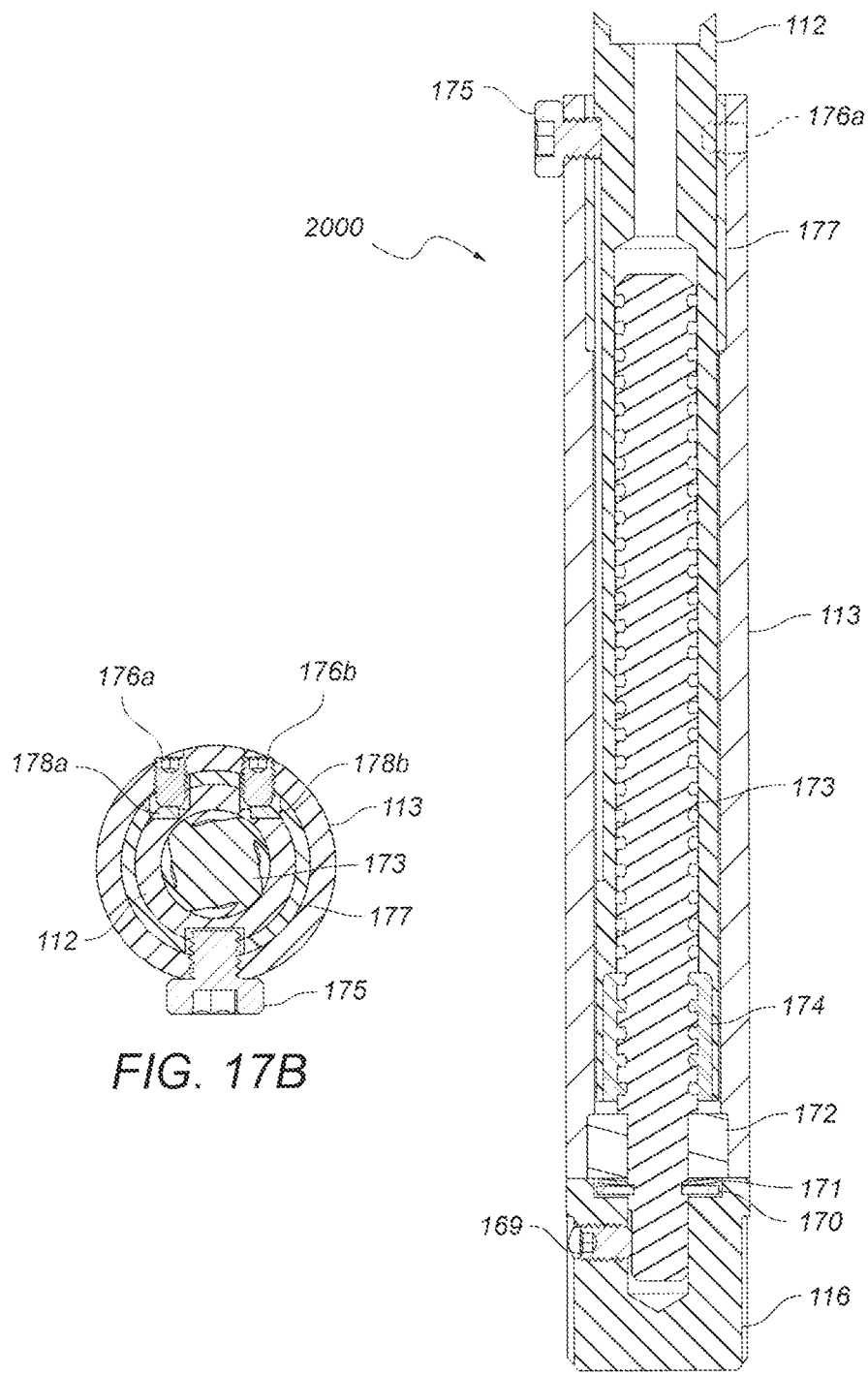
FIG. 17A depicts, in accordance with an embodiment of the invention, a cross-sectional view of the long axis of positioning arm 2000.
FIG. 17B depicts, in accordance with an embodiment of the invention, a cross sectional view of the short axis of positioning arm 2000.

FIG. 3 shows an exploded view of stereotactic apparatus 100, in which the attachment of guiding arm 1000 to positioning arm 2000 is shown to be accomplished by securing screw 133 of guiding arm 1000 to receiving socket 134 of positioning arm 2000. FIG. 3 also shows that positioning arm 2000 traverses a cylindrical opening through upper collar 115 of cross clamp 132. FIG. 15 shows a partially exploded view of positioning arm 2000, in which the assembly of collar 174, threaded shaft 173, bushing 172, curved spring washer 171, radial ring 170, set screw 169, and dial 116 is shown. FIG. 15 also shows outer nested component 113 and inner nested component 112 of positioning arm 2000. FIG. 16 shows the assembly of inner 112 and outer 113 nesting components of positioning arm 2000. Specifically, screw 175 and set screws 176a and 176b traverse outer nested component 113 and inner stabilizing collar 177. The set screws 176a and 176b then contact supporting elements 178a and 178b, respectively, which in turn rest on the flat portions of elongated L-shaped grooves 179a and 179b, respectively. This arrangement allows supporting elements 178a and 178b (and screw 175) to constrain motion of inner nesting component 112 of positioning arm 2000, and adds to the stability and control of its telescoping motion. Cross-sectional views of positioning arm 2000 are depicted in FIGS. 17A and B.

Figure 4:
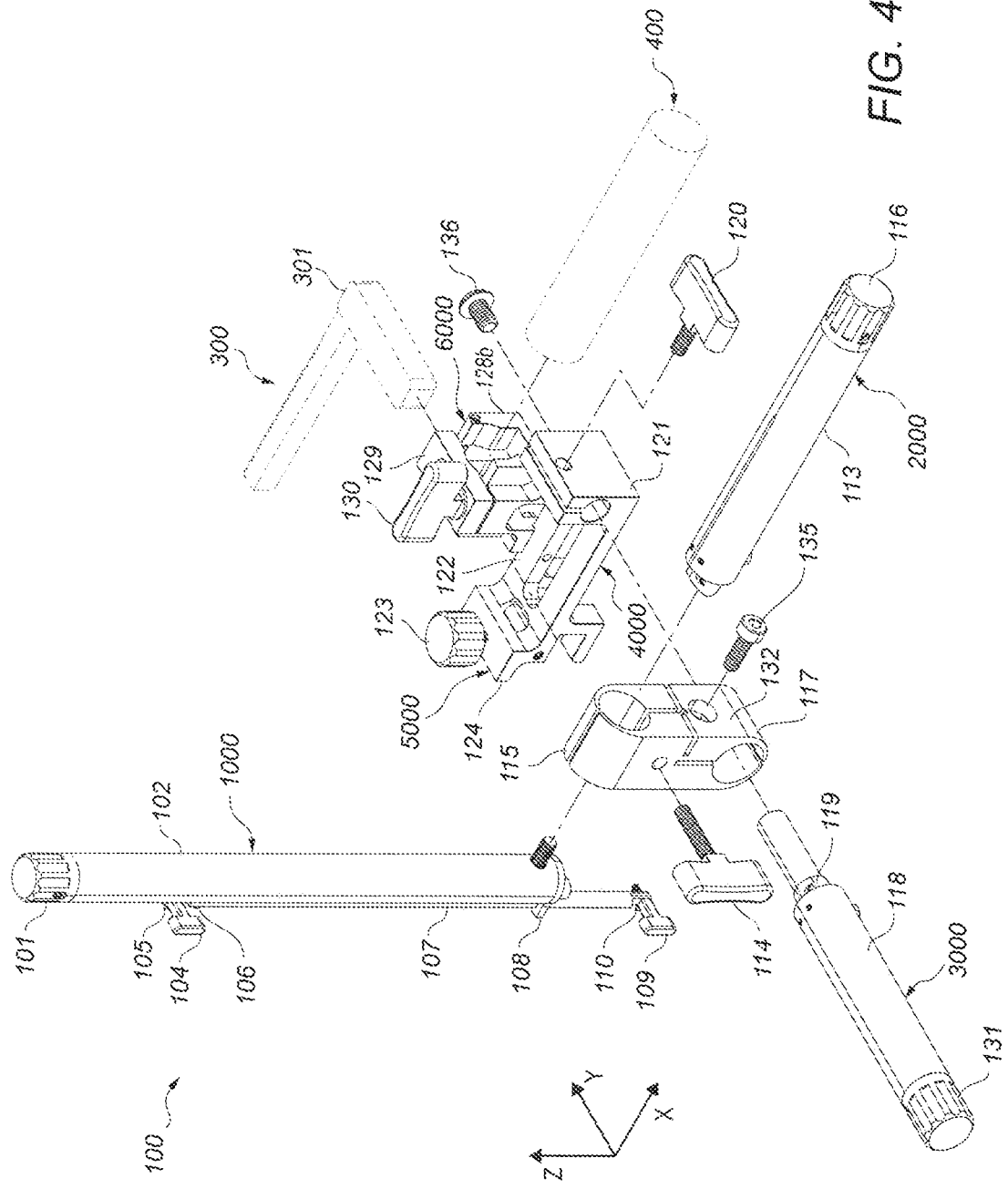
FIG. 4 depicts, in accordance with an embodiment of the invention, a partially exploded view of stereotactic apparatus 100.
Figure 13:
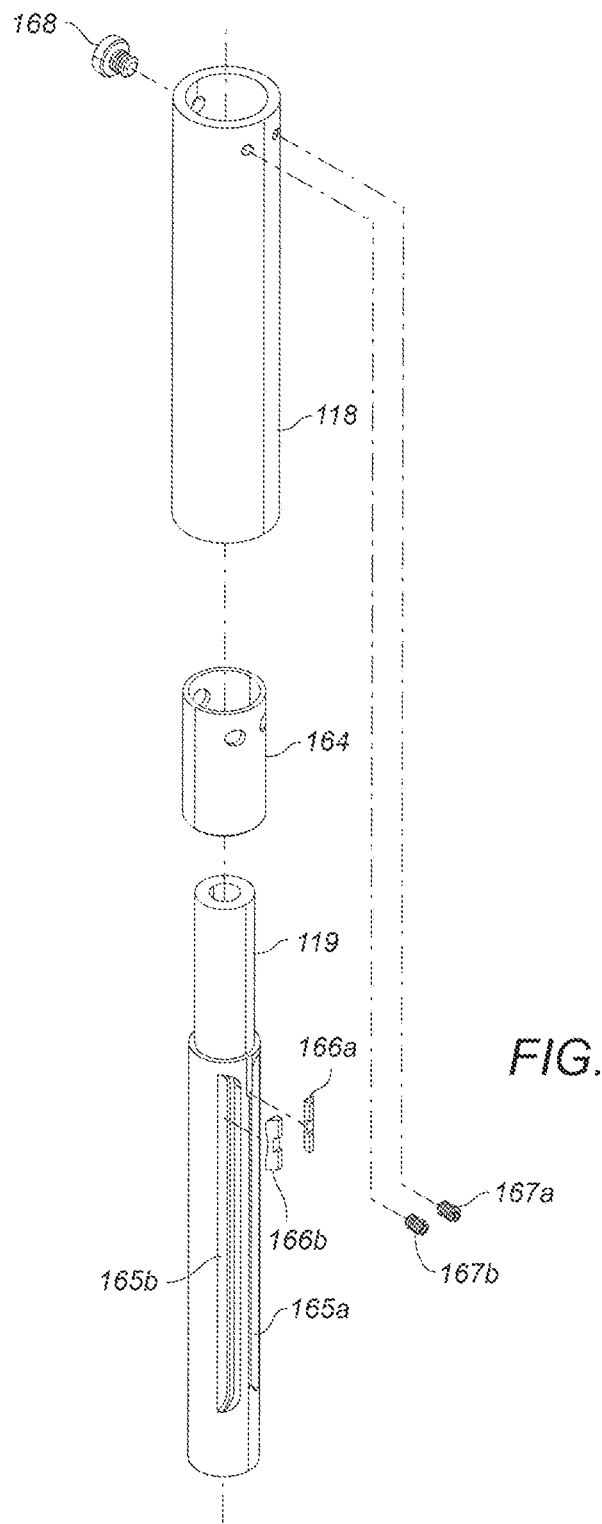
FIG. 13 depicts, in accordance with an embodiment of the invention, an exploded view of a portion of connecting arm 3000.
Figure 14:
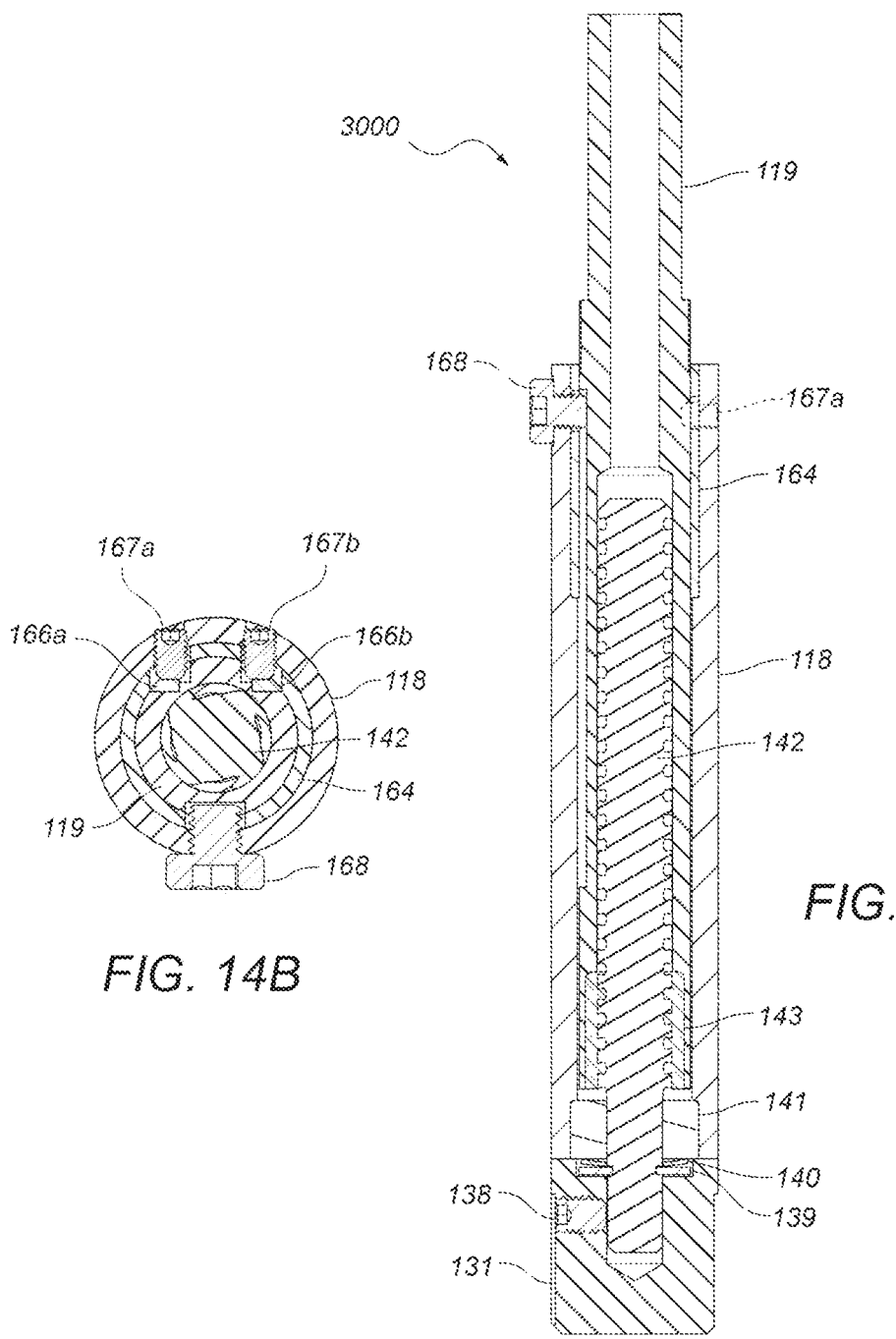
FIG. 14A depicts, in accordance with an embodiment of the invention, a cross-sectional view of the long axis of connecting arm 3000.
FIG. 14B depicts a cross-sectional view of the short axis of connecting arm 3000.

In addition to guiding arm 1000 and positioning arm 2000, FIG. 3 also shows connecting arm 3000 of stereotactic apparatus 100 with outer nested element 118 and inner nested element 119. FIG. 3 shows connecting arm 3000 traverses the cylindrical opening of lower collar 117 of cross clamp 132. FIG. 3 also shows that connecting arm 3000 traverses a cylindrical opening in clamp 121, and is fastened to end screw 136. An alternate view of these components is demonstrated in FIG. 4. FIG. 4 also depicts knob 120 and screw 135, which can each be tightened to secure connecting arm 3000 in clamp 121 and lower collar 117 (of cross clamp 132), respectively. FIG. 13 shows the assembly of inner 119 and outer 118 nesting components of connecting arm 3000. Screw 168 and set screws 167a and 167b traverse outer nested component 118 and inner stabilizing collar 164. Set screws 167a and 167b then contact supporting elements 166a and 166b, respectively, which in turn rest on the flat portion of elongated L-shaped grooves 165a and 165b, respectively. This arrangement allows supporting elements 166a and 166b (and screw 168) to constrain motion of inner nesting element 119, and adds to the stability and control of its telescoping motion. Cross-sectional views of attaching arm 3000 are depicted in FIGS. 14A and B.

FIG. 3 also shows a view of securing arm 4000, which includes clamp 121, body 122, and retractor attaching clamp 5000. Retractor attaching clamp 5000 is formed by knob 123, stabilizing screw 126 (which passes through upper lip 124 of clamp 5000), upper stabilizing arms 125a and 125b, and lower stabilizing arms 127a and 127b. An exploded view of securing arm 4000 is shown in FIG. 21. In this view, incorporation of set screw 162 and rod 161 in the context of the other components of the clamp can be seen.

FIG. 3 further shows side clamp 6000 of stereotactic apparatus 100. Side clamp 6000 includes tray arms 128a and 128b, and hinged top 129. Hinged top 129 includes an opening through which a portion of an object clamped by side clamp 6000 (such as elongated object 400 shown in FIG. 1) can be viewed.

Figure 7:
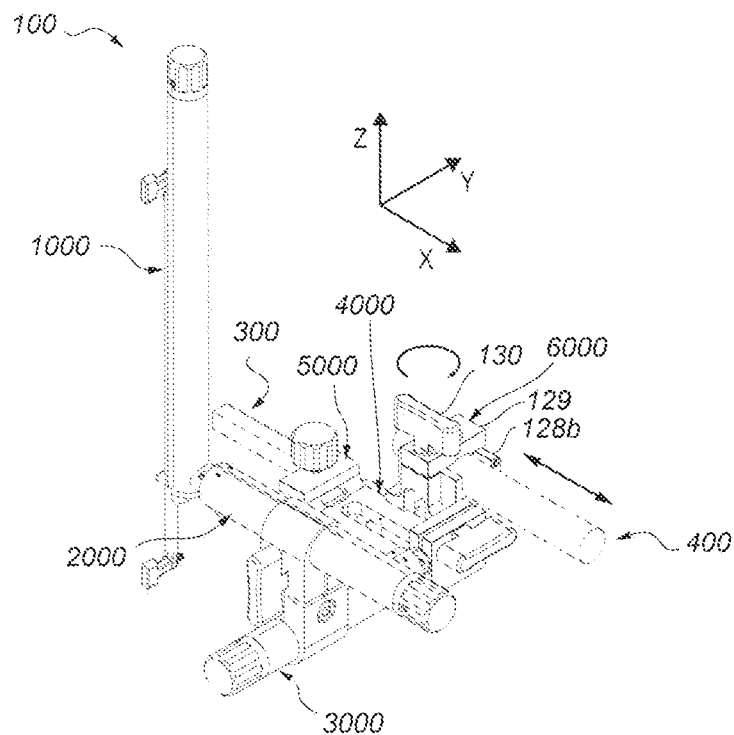
FIG. 7 depicts, in accordance with an embodiment of the invention, loosening knob 130 allows for adjustment of the position of cylindrical object 400 along the x-axis.
Figure 11:
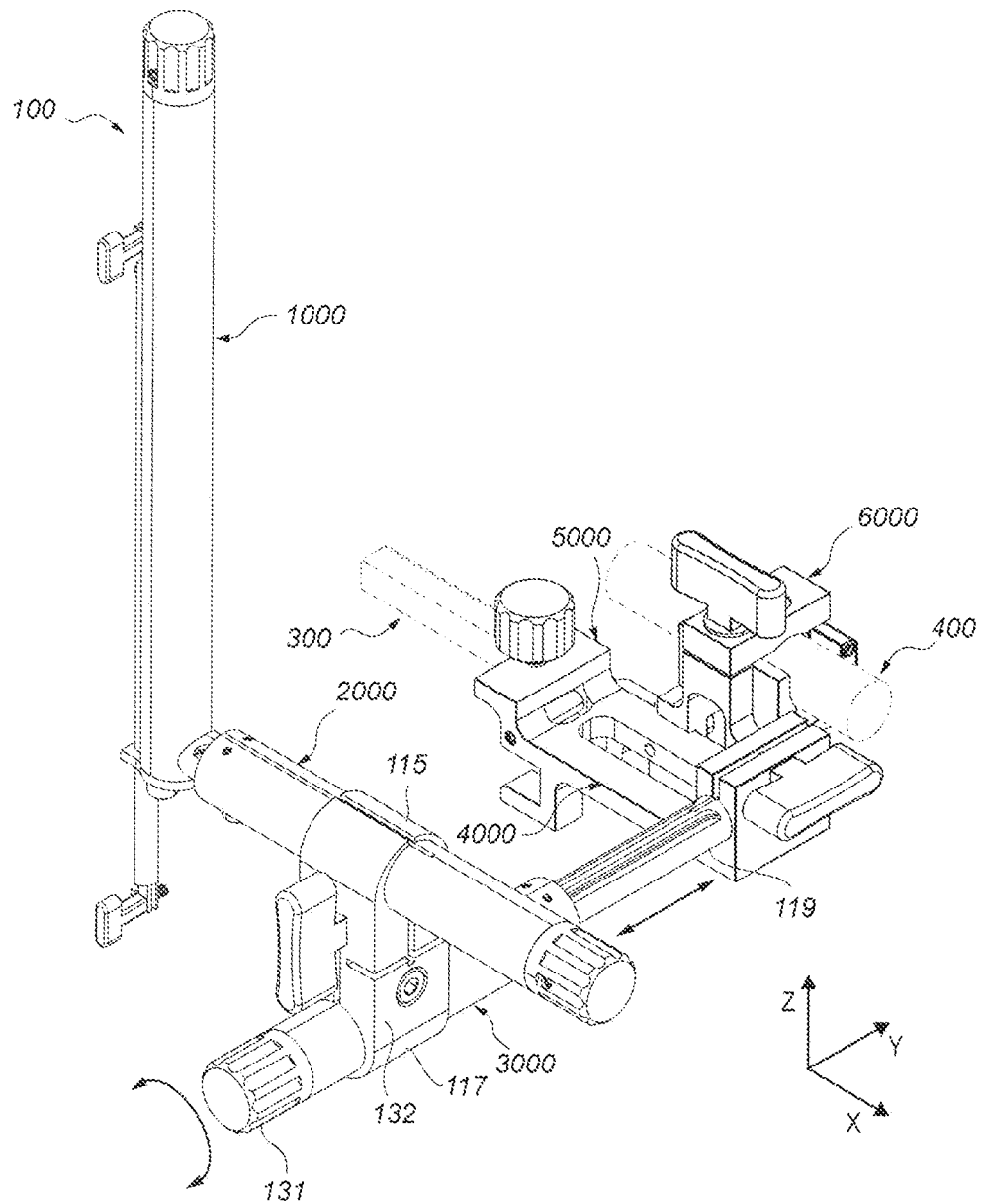
FIG. 11 depicts, in accordance with an embodiment of the invention, rotating dial 131 causes telescoping motion of inner nesting element 119 of connecting arm 3000.

Turning now to the various possible adjustments and orientations of the arms (and components thereof) of stereotactic apparatus 100 shown in FIGS. 5-11. FIG. 5 shows rotation of knob 114 loosens upper collar 115 of cross clamp 132, thereby allowing adjustment of the position of positioning arm 2000 along the x-axis. FIG. 8 shows that rotation of knob 114 (and associated loosing of upper collar 115 of cross clamp 132) allows for rotation of positioning arm 2000 along the x-axis, which translates into motion of guiding arm 1000 along the y-z plane. FIG. 6 shows that rotation of screw 135 results in loosening lower collar 117 of cross clamp 132, which allows for adjustment of the position of positioning arm 2000 along the y-axis. FIG. 9 shows that rotation of screw 135 (and associated loosening of lower collar 117 of cross clamp 132) allows for rotation of cross clamp 132 along the y-axis, which translates into motion of guiding arm 1000 along the x-z plane. FIG. 7 demonstrates that rotation of knob 130 (and associated loosening of side clamp component 129) allows for adjustment of the position of cylindrical object 400 along the x-axis. FIG. 10 shows that rotation of dial 116 is associated with telescoping of positioning arm 2000 along the x-axis. FIG. 10 also shows that rotation of dial 101 is associated with motion of instrument attachment component 107 of guiding arm 1000 along the z-axis. FIG. 11 shows that rotation of dial 131 is associated with telescoping of connecting arm 3000 along the y-axis.

Example 2

Stereotactic Apparatus without Side Clamp

Figure 1C:
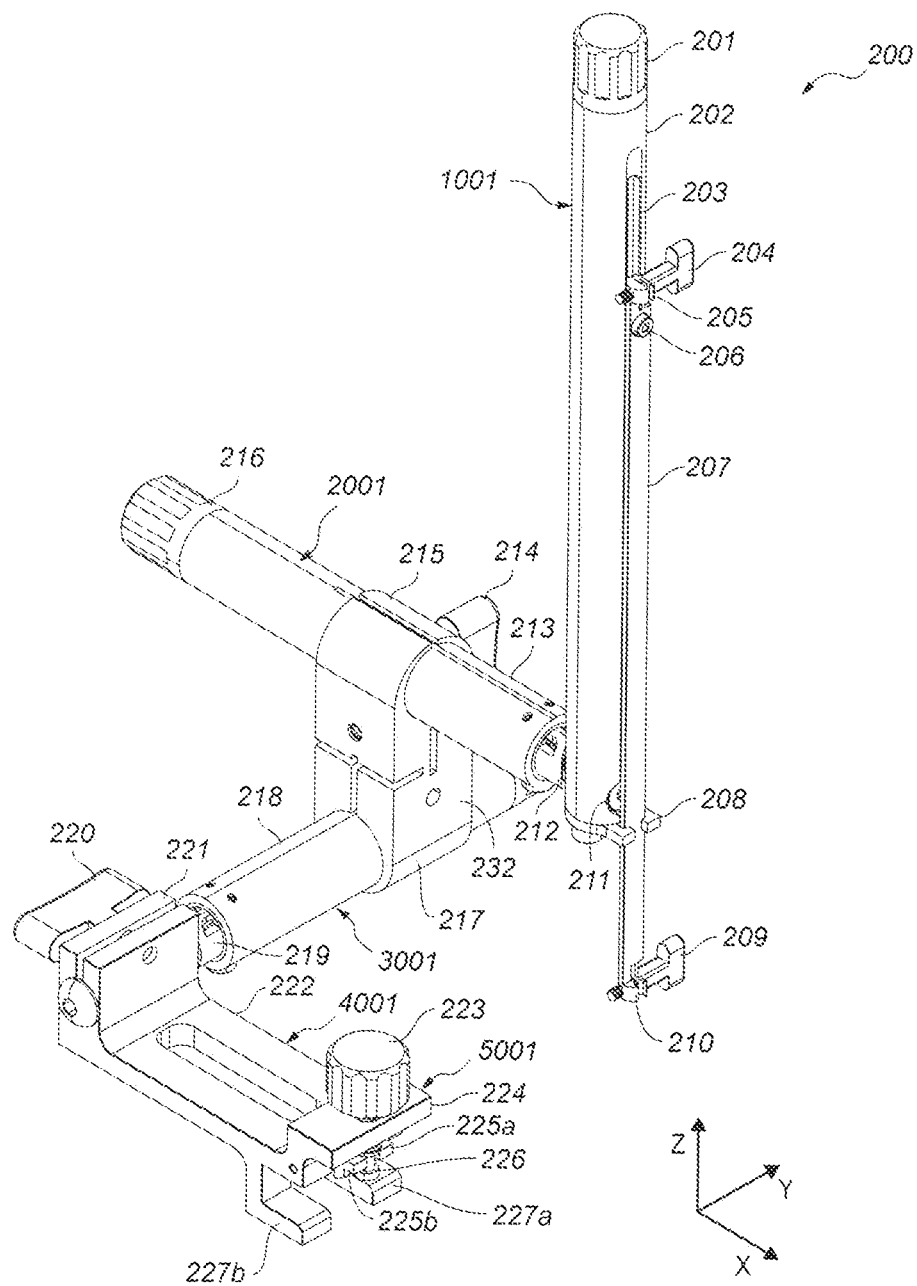
FIG. 1C depicts stereotactic apparatus 200.
Figure 1D:
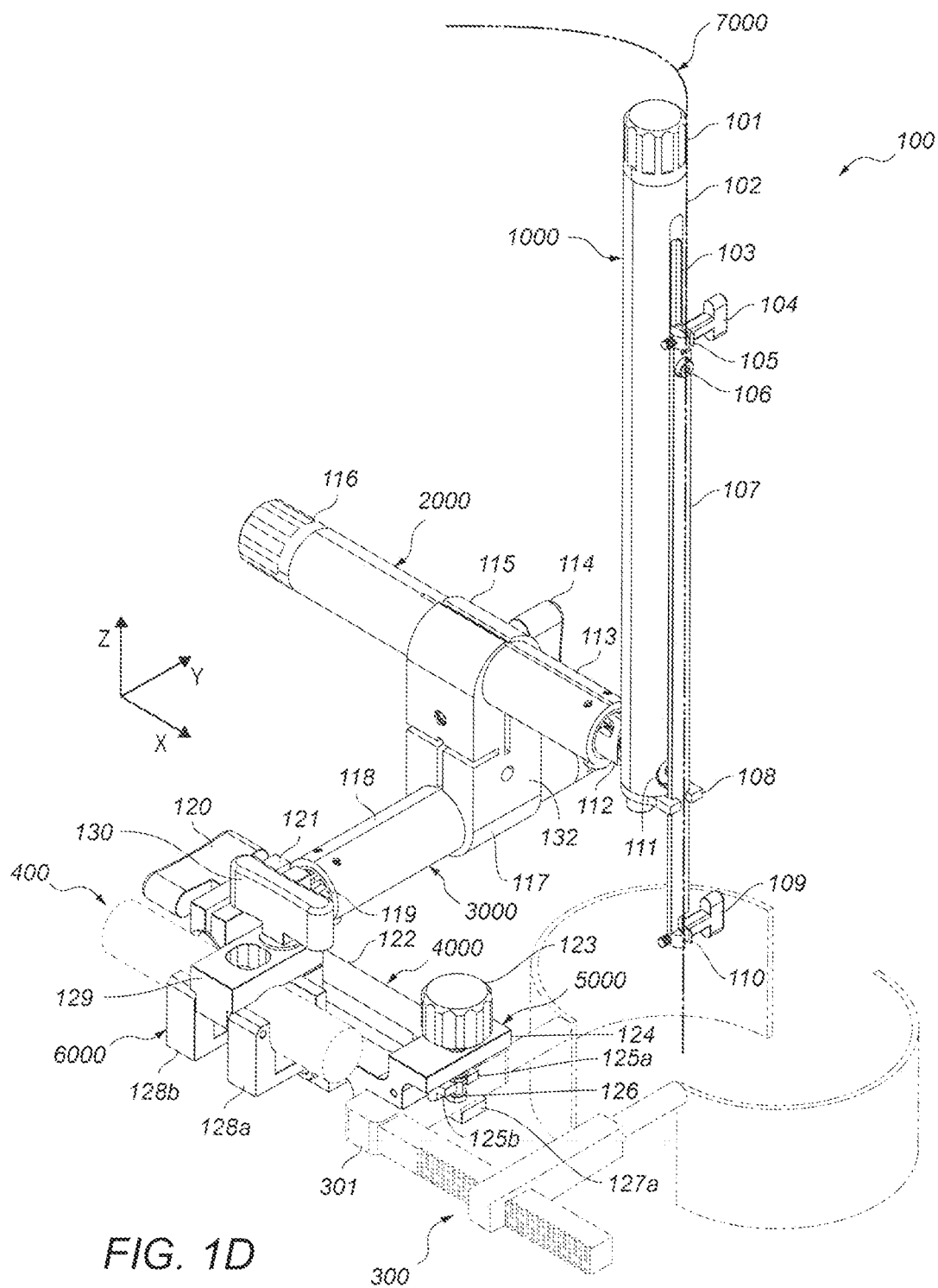
FIG. 1D depicts stereotactic apparatus 100 attached to cylindrical object 400 and tissue retractor 300. Instrument 7000 is shown attached to guiding arm 1000 of stereotactic apparatus 100, and extending downward along the z-axis between the arms of tissue retractor 300.
Figure 2A:
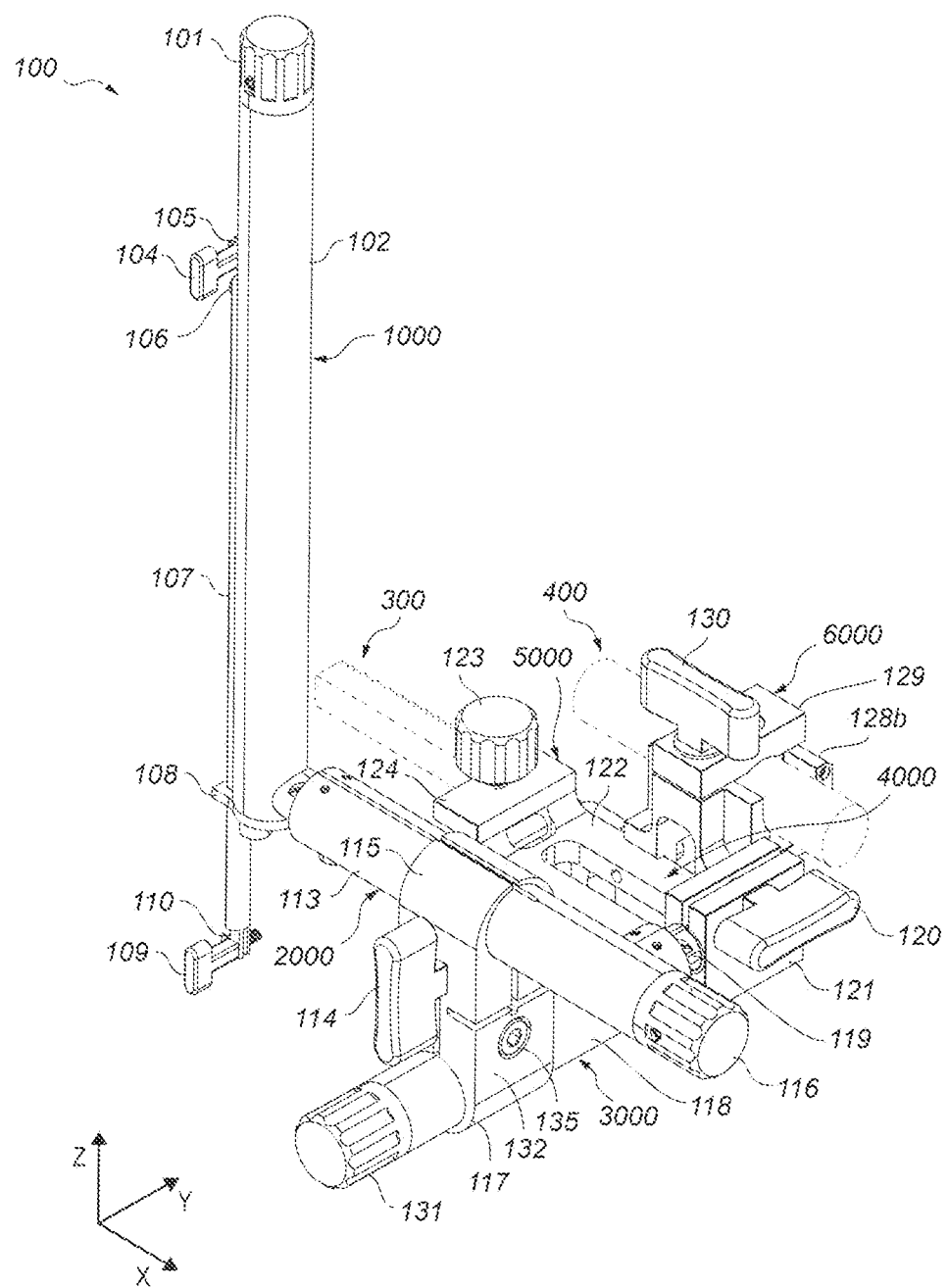
FIG. 2A depicts, in accordance with an embodiment of the invention, stereotactic apparatus 100. Tissue retractor 300 and cylindrical object 400 are shown.
Figure 2B:
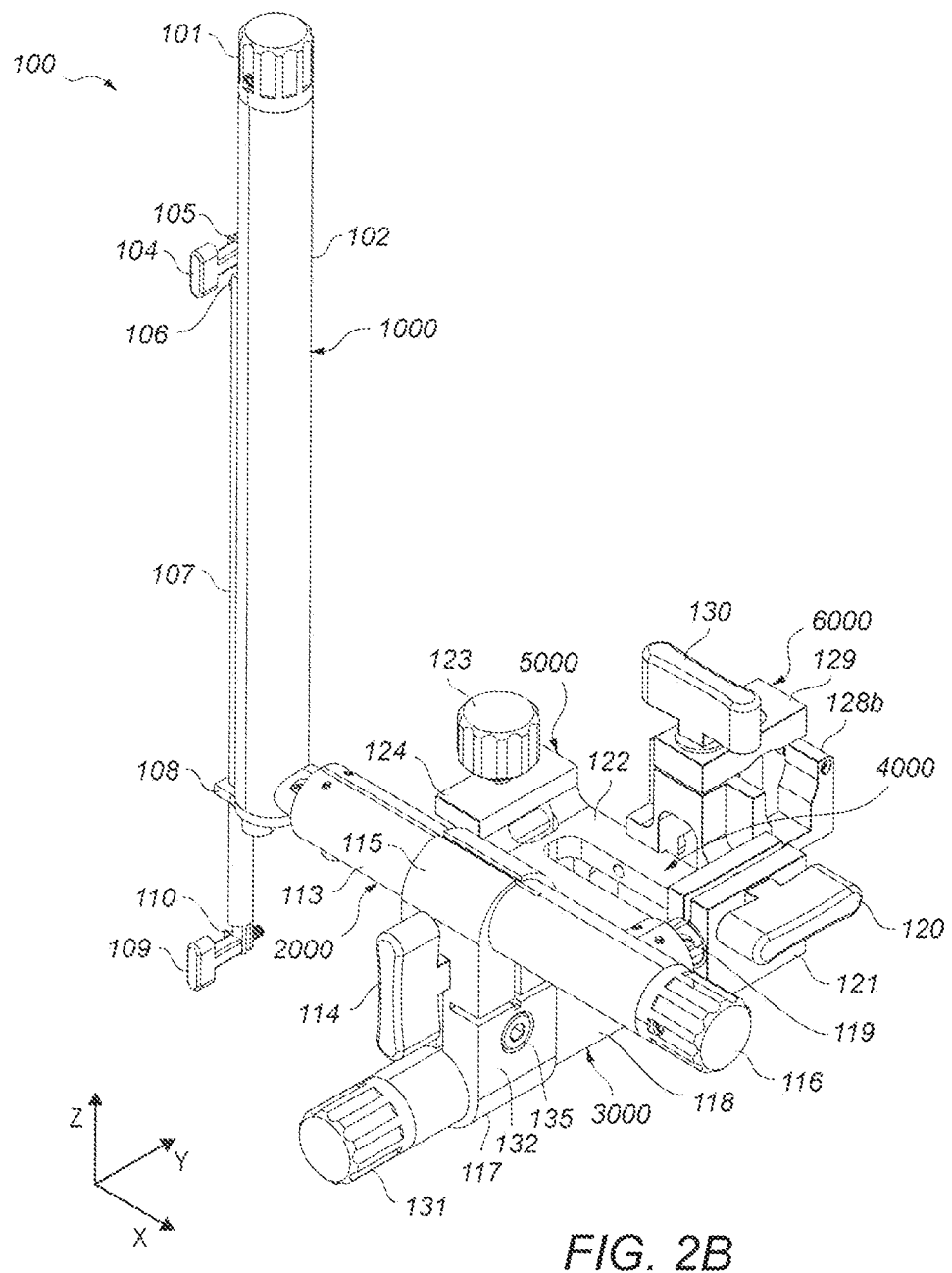
FIG. 2B depicts an alternate view of stereotactic apparatus 100.
Figure 2C:
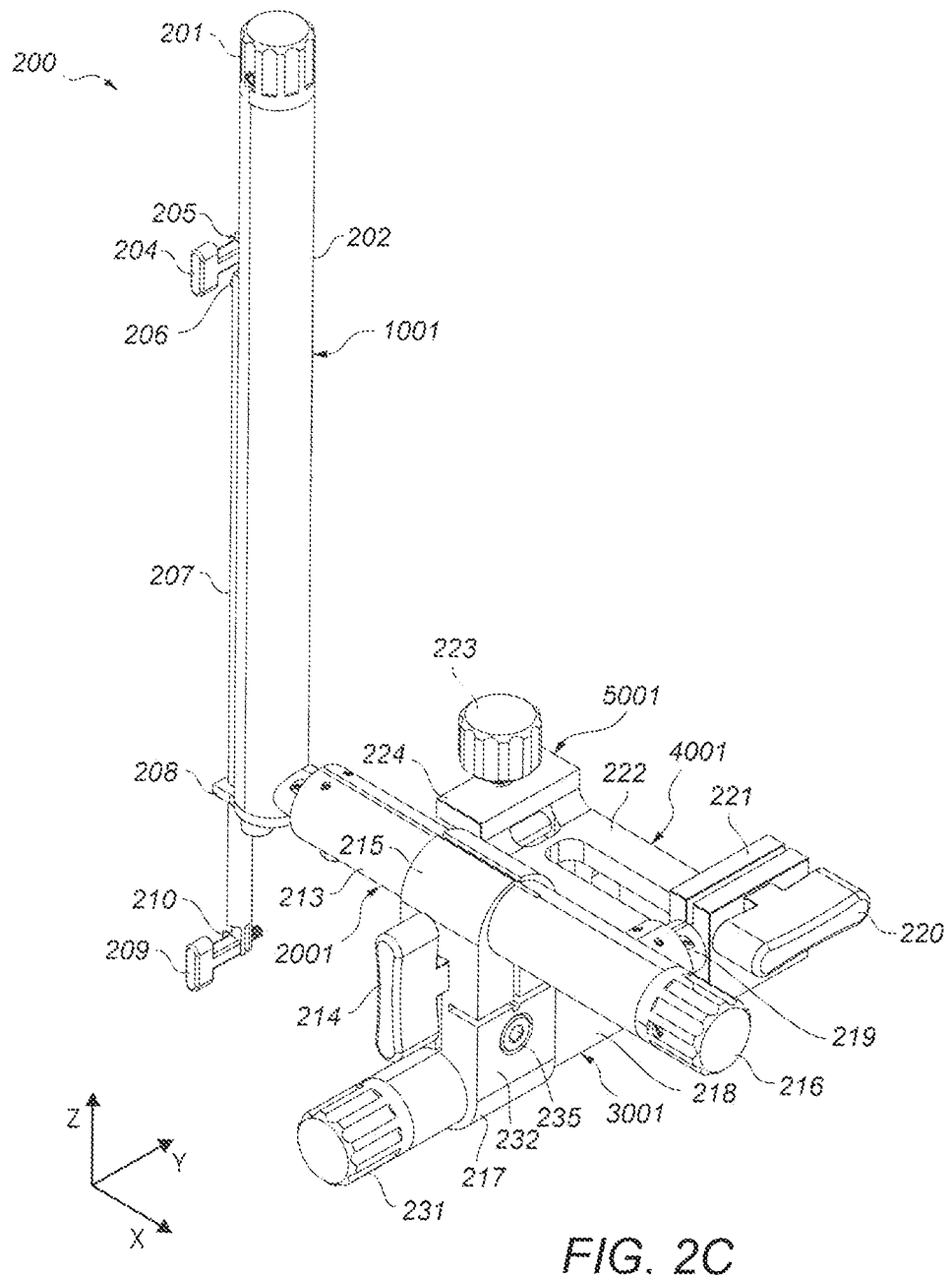
FIG. 2C depicts an alternate view of stereotactic apparatus 200.

FIGS. 1C and 2C depict stereotactic apparatus 200, which includes the same components as stereotactic apparatus 100, with the exception of the side clamp 128 depicted in stereotactic apparatus 100. Stereotactic apparatus 200 also functions in the same way as stereotactic apparatus 100, with the exception of the functions that relate to side clamp 128.

Example 3

Surgical Procedure

A single level laminectomy can be performed on the L4 vertebral segment. Standard anesthetic/preoperatory techniques are used and the patient is positioned prone. A 4 cm incision is made at the midline above the L4 spinous process. Cutting electrocautery is used to cut the fascia and extend the incision to the spinous process, as well as achieving hemostasis of any small hemorrhages from the incision site. At this point a Weitlaner retractor can be used to keep the incision open. A bilateral sub-periosteal dissection is performed carefully by elevating the muscles and periosteum off of the lamina. Cutting electrocautery is used to facilitate the dissection. The spinous process is then removed using a Leksell rongeur. A high-speed drill is used to thin the lamina laterally. The lamina is then lifted and the ligamentous attachment is cut to release the lamina. Kerrison rongeurs are then be used to extend the laminectomy or clean up any left over bone fragments. In this case, the Medtronic Mast Quadrant retractor system is used. The Weitlaner retractor is removed, and the Mast Quadrant retractor blades are inserted into the incision and attached to the retractor system flex arms. The retractor is opened rostrocaudally to achieve maximum tissue spread. The mediolateral retractor is used in order to keep muscle out of the field. A ~2.5 cm dura incision is made using an #11 blade and a dural guide to prevent spinal cord injury. Using 4-0 Neurolon the dura is then tacked at the four corners of the opening to be able to visualize the nerve roots and facilitate injections. At this point, inventive device 100 is attached to the Mast Quadrant using clamp 5000. Coronal and saggital angles can be adjusted on the device depending on the spinal cord target using the adjustment mechanisms described above. In this case, the ventral horn is targeted, so a 90-degree (orthogonal) angle of the surgical instrument (needle, cannula, etc) to the spinal cord is established. The surgical instrument (needle, cannula) can now be attached to the device. Using the dials of the device, rostrocaudal and mediolateral movement can be achieved to find accurate placement to the target. The surgical instrument is then positioned into the spinal cord using the ventral rostral movement provided by dial 101 to the appropriate depth. Imaging (CT, MRI, Ultrasound, and the like) can be used to help position the device in all planes (coronal and saggital angle, rostrocaudal, mediolateral and dorsoventral positioning). When the surgical instrument (needle) is in position, the therapeutic agent (neural progenitor cells) can be infused into the spinal cord target. The surgical instrument is then returned to the starting position and can then be repositioned for subsequent injections. Once all of the injections/infusions are completed, the surgical instrument can be removed, followed by the device. The dura tacks can then be cut and the retractor system removed. The incision can then be closed in four layers. The dura is closed with a running stitch using a 4-0 neurolon. Once it's closed, a valsalva maneuver can be performed to ensure it's watertight and there's no cerebrospinal fluid leakage. The deep muscle layer is closed with a 0 Vycril suture as well as the Muscle fascia. The dermal layer is closed using a 3-0 vycril and finally the skin is closed using a locked running stitch with 2-0 nylon.

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Certain embodiments of this application are described herein, including the best mode known to the inventors for carrying out the application. Variations on those embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed is:

1. An apparatus, comprising:
   a securing arm comprising a first end, a second end, a long axis, and a short axis;
   a connecting arm comprising a first end, a second end, a long axis, and a short axis;
   a positioning arm comprising a first end, a second end, a long axis, and a short axis; and
   a guiding arm comprising a first end, a second end, a long axis, and a short axis;
   wherein the first end of the connecting arm is attached to the second end of the securing arm, the second end of the connecting arm is attached to the first end of the positioning arm, and the positioning arm is attached at its second end to the second end of the guiding arm,
   wherein rotation of the positioning arm around the long axis of the positioning arm translates into motion of the guiding arm along a plane perpendicular to the long axis of the positioning arm, and
   wherein the guiding arm further comprises an instrument attaching component configured to slide along the long axis of the guiding arm, wherein the sliding motion is controlled by a dial and wherein the instrument attaching component is configured to attach to a cannula.

2. The apparatus of claim 1, wherein the securing arm further comprises one or more clamps on its first end, and wherein the one or more clamps are configured to attach to an arm of a tissue retractor.

3. The apparatus of claim 1, wherein:
   the instrument attaching component comprises one or more clamps configured to clamp the cannula;
   the guiding arm further comprises an elongated channel situated along the long axis of the guiding arm; and
   the instrument attaching component is configured to slide along the elongated channel.

4. The apparatus of claim 1, wherein the connecting arm comprises elongated nesting elements that allow for telescoping motion in the direction of its long axis, such that the length of the connecting arm can be increased or decreased.

5. The apparatus of claim 4, wherein the positioning arm comprises elongated nesting elements that allow for telescoping motion in the direction of its long axis, such that the length of the positioning arm can be increased or decreased.

6. The apparatus of claim 5, wherein the telescoping motion of the connecting arm is controlled by rotation of a dial situated at its second end.

7. The apparatus of claim 6, wherein the telescoping motion of the positioning arm is controlled by rotation of a dial situated at its first end.

8. The apparatus of claim 1, further comprising a side clamp attached to the securing arm, wherein the side clamp is configured to attach to an elongated object.

9. The apparatus of claim 8, wherein the securing arm is removably attached to the connecting arm.

10. The apparatus of claim 9, wherein:
    the positioning arm is removably attached to the connecting arm and/or the guiding arm; and
    the positioning arm is configured to allow rotation around the long axis of the positioning arm by loosening of a collar by rotating a knob.

11. The apparatus of claim 10, wherein the side clamp is removably attached to the securing arm.

12. The apparatus of claim 11, wherein the elongated object is a device selected from the group consisting of: a liquid reservoir, a gas reservoir, a pump, an imaging device, and combinations thereof.

13. A system, comprising the apparatus of claim 1 and a tissue retractor attached to the securing arm of the apparatus by one or more clamps of the securing arm.

14. The system of claim 13, wherein the cannula comprises a needle situated at the end thereof.

15. The system of claim 14, wherein the cannula and needle are configured to inject cells into a region of interest in a subject's body.

16. The system of claim 15, wherein the cannula contains a quantity of neural progenitor cells.

17. The system of claim 16, wherein the neural progenitor cells express glial cell line derived neurotrophic factor.

18. The system of claim 17, wherein the region of interest is the subject's spine.

19. The system of claim 18, further comprising a liquid reservoir and a pump connected thereto, wherein the liquid reservoir and pump are attached to a side clamp attached to the securing arm.

20. A method for performing a surgical procedure on a subject, comprising attaching the apparatus of claim 1 to an arm of a tissue retractor that is engaged in an incision in the subject's body, and guiding the cannula attached to the guiding arm of the apparatus through the incision in the subject's body.

21. The method of claim 20, wherein the cannula comprises a needle situated at the end thereof.

22. The method of claim 21, wherein the cannula and needle are configured to inject cells into a region of interest in the subject's body.

23. The method of claim 22, wherein the region of interest is the subject's spine.

24. The method of claim 23, wherein the cells are neural progenitor cells.

25. The method of claim 24, wherein the subject has been diagnosed with amyotrophic lateral sclerosis (ALS).

26. The method of claim 25, further comprising performing imaging of the region of interest in the subject's body.

27. The method of claim 26, wherein the imaging performed is selected from the group consisting of computed tomography (CT), magnetic resonance imaging (MM), ultrasound, and combinations thereof.

28. The method of claim 25, further comprising injecting neural progenitor cells expressing glial cell line derived neurotrophic factor into the subject's spine.

* * * * *